United States Patent
Trepagnier et al.

(10) Patent No.: US 6,721,582 B2
(45) Date of Patent: Apr. 13, 2004

(54) NON-INVASIVE TISSUE GLUCOSE LEVEL MONITORING

(75) Inventors: Pierre Trepagnier, Medford, MA (US); Jenny Freeman, Weston, MA (US); James Mansfield, Boston, MA (US); Derek Brand, Brighton, MA (US); Michael J. Hopmeier, Mary Ester, FL (US); Nikiforos Kollias, Skillman, NJ (US)

(73) Assignee: Argose, Inc., Waltham, MA (US)

( * ) Notice: Subject to any disclaimer, the term of this patent is extended or adjusted under 35 U.S.C. 154(b) by 0 days.

(21) Appl. No.: 09/785,547

(22) Filed: Feb. 20, 2001

(65) Prior Publication Data

US 2002/0016534 A1 Feb. 7, 2002

Related U.S. Application Data

(63) Continuation-in-part of application No. 09/287,486, filed on Apr. 6, 1999.
(60) Provisional application No. 60/183,358, filed on Feb. 18, 2000.

(51) Int. Cl.[7] .................................................. A61B 5/00
(52) U.S. Cl. ........................................ 600/316; 600/317
(58) Field of Search ................................. 600/309–310, 600/322–326, 316, 473, 476

(56) References Cited

U.S. PATENT DOCUMENTS

| | | | |
|---|---|---|---|
| 3,837,339 A | 9/1974 | Aisenberg et al. | |
| 4,206,755 A | 6/1980 | Klein | |
| 4,515,165 A | 5/1985 | Carroll | |
| 4,655,225 A | 4/1987 | Dähne et al. | |
| 4,721,677 A | 1/1988 | Clark, Jr. | 435/291 |
| 4,866,644 A | 9/1989 | Shenk et al. | 364/571.02 |
| 4,979,509 A | 12/1990 | Hakky | |
| 5,001,054 A | 3/1991 | Wagner | 435/14 |
| 5,009,230 A | 4/1991 | Hutchinson | |
| 5,101,814 A | 4/1992 | Palti | |
| 5,115,137 A | 5/1992 | Andersson-Engels et al. | 250/461.2 |
| 5,190,041 A | 3/1993 | Palti | |
| 5,202,424 A | 4/1993 | Vlassara et al. | 530/395 |

(List continued on next page.)

FOREIGN PATENT DOCUMENTS

| | | | |
|---|---|---|---|
| EP | 0063431 | 10/1982 | G01N/21/31 |
| EP | 0623307 | 11/1994 | A61B/5/00 |
| EP | 0663591 | 7/1995 | G01N/21/47 |
| EP | 0783867 | 7/1997 | A61B/5/103 |
| GB | 2300045 | 10/1986 | A61B/5/00 |
| WO | WO92/15008 | 9/1992 | G01N/21/65 |
| WO | WO93/17621 | 9/1993 | |
| WO | WO94/10901 | 5/1994 | A61B/5/00 |
| WO | WO95/06431 | 3/1995 | A61B/5/00 |
| WO | WO96/07889 | 3/1996 | G01N/21/64 |
| WO | WO97/48331 | 12/1997 | |
| WO | WO99/27848 | 6/1999 | |
| WO | WO99/51142 | 10/1999 | |

OTHER PUBLICATIONS

M. Kathleen Alam et al. "Characterization of pH Variation in Lysed Blood by Near–Infrared Spectroscopy," Applied Spectroscopy, vol. 52, No. 3, pp. 393–399, 1998.

(List continued on next page.)

*Primary Examiner*—Max F. Hindenburg
*Assistant Examiner*—Matthew Kremer
(74) *Attorney, Agent, or Firm*—Mintz Levin Cohn Ferris Glovsky & Popeo, PC; Ivor R. Elrifi; Christina K. Stock

(57) ABSTRACT

Instruments and methods are described for performing non-invasive measurements of analyte levels and for monitoring, analyzing and regulating tissue status, such as tissue glucose levels.

26 Claims, 8 Drawing Sheets

U.S. PATENT DOCUMENTS

| | | | |
|---|---|---|---|
| 5,209,231 A | 5/1993 | Cote et al. | |
| 5,291,887 A | 3/1994 | Stanley et al. | |
| 5,313,941 A | 5/1994 | Braig et al. | |
| 5,318,023 A | 6/1994 | Vari et al. | |
| 5,341,805 A | 8/1994 | Stavridi et al. | |
| 5,342,789 A | 8/1994 | Chick et al. | 436/501 |
| 5,368,028 A | 11/1994 | Palti | |
| 5,370,114 A | 12/1994 | Wong et al. | |
| 5,372,135 A | 12/1994 | Mendelson et al. | |
| 5,377,676 A | 1/1995 | Vari et al. | |
| 5,379,764 A | 1/1995 | Barnes et al. | |
| 5,452,716 A | 9/1995 | Clift | |
| 5,459,677 A | 10/1995 | Kowalski et al. | 364/571.02 |
| 5,492,118 A | 2/1996 | Gratton et al. | |
| 5,497,772 A | 3/1996 | Schulman et al. | |
| 5,507,288 A | 4/1996 | Böcker et al. | |
| 5,515,847 A | 5/1996 | Braig et al. | |
| 5,533,509 A | 7/1996 | Koashi et al. | |
| 5,553,616 A | 9/1996 | Ham et al. | |
| 5,559,728 A | 9/1996 | Kowalski et al. | 364/571.02 |
| 5,569,186 A * | 10/1996 | Lord et al. | 600/316 |
| 5,593,390 A | 1/1997 | Castellano et al. | 604/187 |
| 5,596,992 A | 1/1997 | Haaland et al. | |
| 5,601,079 A | 2/1997 | Wong et al. | |
| 5,657,754 A | 8/1997 | Rosencwaig | |
| 5,666,956 A | 9/1997 | Buchert | |
| 5,676,143 A | 10/1997 | Simonsen et al. | |
| 5,712,101 A | 1/1998 | Bucala | 435/7.1 |
| 5,713,353 A | 2/1998 | Castano | |
| 5,850,623 A | 12/1998 | Carman, Jr. et al. | 702/28 |
| 5,857,462 A | 1/1999 | Thomas et al. | |
| 6,016,435 A | 1/2000 | Maruo et al. | 600/316 |
| 6,088,605 A | 7/2000 | Griffith et al. | 600/316 |
| 6,175,752 B1 * | 1/2001 | Say et al. | 600/345 |
| 6,232,609 B1 | 5/2001 | Snyder et al. | |
| 6,505,059 B1 * | 1/2003 | Kollias et al. | 600/316 |
| 2002/0143243 A1 | 10/2002 | Georgakoudi et al. | |

OTHER PUBLICATIONS

M. Kathleen Alam et al. "Measurement of pH in Whole Blood by Near–Infrared Spectroscopy," Applied Spectroscopy, vol. 53, No. 3, pp. 316–323, 1999.

John T. Diffee, "Tobacco Analysis by NIR Spectroscopy," R.J. Reynolds Tobacco Company, Winston–Salem, North Carolina, 1992.

Bruulsema et al. "Correlation Between Blood Glucose Concentration in Diabetics and Noninvasively Measured Tissue Optical Scattering Coefficient," Optics Letters, vol. 22, No. 3, Feb. 1, 1997.

Klonoff, "Noninvasive Blood Glucose Monitoring," Diabetes Care, vol. 20, No. 3, Mar. 1997.

Kohl et al., "Influence of Glucose Concentration on Light Scattering in Tissue–Simulating Phantoms," Optics Letters, vol. 19, No. 24, Dec. 15, 1994.

Kollias et al., "Endogenous Skin Fluorescence Includes Bands that may Serve as Quantitative Markers of Aging and Photoaging," Journal of Investigative Dermatology, vol. 111, No. 5, Nov. 1998.

N. Kollias et al., Journal of Investigative Dermatology, 111:776–81, 1998.

Maier et al., "Possible Correlation Between Blood Glucose Concentration and the Reduced Scattering Coefficeint of Tissues in the Infrared," Optics Letters, vol. 19, No. 24, Dec. 15, 1994.

V.M. Monnier et al., "Skin Collagen Glycation, Glycoxidation, and Crosslinking Are Lower in Subjects With Long–Term Intesive Versus Conventional Therapy of Type 1 Diabetes" Diabetes 48:870–880, 1999.

Qu and Wilson, "Monte Carlo Modeling Studies of the Effect of Physiological Factors and Other Analytes on the Determination of Glucose Concentration In Vivo by Near Infrared Optical Absorption and Scattering Measurements," Journal of Biomedical Optics, vol. 2, No. 3, Jul. 1997.

Sannes, "The Outlook for Noninvasive and Minimally Invasive Glucose Testing," Decision Resources, Inc. Nov. 1998.

Waynant and Chenault, "Special Issue on Non–Invasive Glucose Monitoring with Optical Techniques," Leos Newsletter, Apr. 1998.

Wang et al., "Multivariate Instrument Standardization," Anal. Chem., vol. 63, pp. 2750–2756 (1991).

Wang et al., "Improvement of Multivariate Calibration through Instrument Standardization," Anal. Chem., vol. 64, pp. 562–564 (1992).

Wang et al., "Additive Background Correction in Multivariate Instrument Standardization," Anal. Chem., vol. 67, pp. 2379–2385 (1995).

Schwartz, Jon A. et al. "Diagnostic potential of laser–induced autoflurescence emission in brain tissue", Journal of Korean Medical Science, vol. 12, No. 2, Apr. 1997, pp. 135–142.

* cited by examiner

NON-INVASIVE TISSUE GLUCOSE LEVEL MONITORING

RELATED APPLICATIONS

The present application is a continuation-in-part of U.S. patent application Ser. No. 09/287,486, filed Apr. 6, 1999, and titled "Non-Invasive Tissue Glucose Level Monitoring." Further, the present invention claims priority to U.S. Provisional Patent Application No. 60/183,358, filed Feb. 18, 2000, and titled "Non-Invasive Tissue Glucose Monitoring."

BACKGROUND OF THE INVENTION

1. Field of the Invention

This invention relates to instruments and methods for performing non-invasive measurements of analyte concentrations and for monitoring, analyzing and regulating tissue status, such as tissue glucose levels.

2. Description of the Background

Diabetes is a chronic life threatening disease for which there is presently no cure. It is the fourth leading cause of death by disease in the United States and at least 175 million people worldwide are estimated to be diabetic. Diabetes is a disease in which the body does not properly produce or respond to insulin. The high glucose concentrations that can result from this affliction can cause severe damage to vital organs, such as the heart, eyes and kidneys.

Type I diabetes (juvenile diabetes or insulin-dependent diabetes mellitus) is the most severe form of the disease, comprising approximately 10% of the diabetes cases in the United States. Type I diabetics must receive daily injections of insulin in order to sustain life. Type II diabetes, (adult onset diabetes or non-insulin dependent diabetes mellitus) comprises the other 90% of the diabetes cases. Type II diabetes is often manageable with dietary modifications and physical exercise, but may still require treatment with insulin or other medications. Because the management of glucose to near-normal levels can prevent the onset and the progression of complications of diabetes. Persons afflicted with either form of the disease are instructed to monitor their blood glucose concentration in order to assure that the appropriate level is achieved and maintained.

Traditional methods of monitoring the blood glucose concentration of an individual require that a blood sample be taken. This method can be painful, inconvenient, costly, and pose the risk of infection. Another glucose measuring method involves urine analysis, which, aside from being inconvenient, may not reflect the current status of the patient's blood glucose because glucose appears in the urine only after a significant period of elevated levels of blood glucose. An additional inconvenience of these traditional methods is that they require testing supplies such as collection receptacles, syringes, glucose measuring devices and test kits. Although disposable supplies have been developed, they are costly and can require special methods for disposal.

Many attempts have been made to develop a painless, non-invasive external device to monitor glucose concentrations. Various approaches have included electrochemical and spectroscopic technologies, such as near-infrared spectroscopy and Raman Spectroscopy. Despite extensive efforts, however, none of these methods has, so far, yielded a non-invasive device or method for the in vivo measurement of glucose that is sufficiently accurate, reliable, convenient and cost-effective for routine use.

The phenomenon of endogenous skin fluorescence, as well as endogenous fluorescence of other biological tissues, has been well documented in the literature. Methods for non-invasively measuring skin fluorescence have been developed and incorporated into commercially available instruments (e.g. Skin Skan or Fluorolog). In skin, important fluorophores include tryptophan-containing proteins, which fluoresces in the 350–450 nm region, and fluorophores associated with collagen cross links, skin oils, NADH, FAD, other flavoproteins, elastin, and quinones, which fluoresce in a broad region from 420 to 650 nm (J. Invest. Dermatol. 111:776–780, 1998, and references therein).

Fluorescence has been used to predict malignancies in tissue, e.g., cervical tissue, bladder tissue, and the buccal cavity. Fluorescence of dyes (fluorescence associated with dyes that selectively bind to biological compounds) has also been used to study in vivo cellular processes.

SUMMARY OF THE INVENTION

The invention overcomes problems and disadvantages associated with current strategies and designs and provides new instruments and methods for monitoring, analyzing and regulating in vivo glucose levels or other analyte levels in an individual.

In one general aspect, the invention features a non-invasive glucose monitoring instrument useful in vivo. The instrument comprises a radiation source, a radiation detector and a processing circuit or analyzing means. The radiation source is capable of directing excitation radiation to a portion of a tissue surface of a patient and emits radiation at at least one wavelength that excites a target in the tissue to emit radiation. The tissue surface may be an exterior or an interior tissue surface of a patient. For example, the surface may be a mucosal area, such as the gums or other mucosal area, the eyeballs, and surrounding areas, such as the eyelids. More preferably, the surface is the patient's skin. Alternately, the tissue surface may be an interior surface such as the serosal or mucosal surface of an organ.

The excited target provides information that can be correlated with the patient's glucose level. More specifically, the radiation emitted from the excited target and received at the tissue surface correlates with the glucose level of the tissue and thus provides a glucose level indication of the patient. A glucose level indication is a quantitative, qualitative or relative measurement that correlates with the blood glucose content or concentration of the patient.

The radiation detector is positioned to receive the radiation emitted from the tissue surface. Radiation received at the surface may be quenched or amplified by one or more matrix, cellular, or mitochondrial components, or any other cellular component reflective of metabolic activity, in the tissue. A processing circuit is operatively connected to the radiation detector that translates emitted radiation to a measurable signal to obtain the glucose level indication. Alternately, analyzing means is operatively connected to the radiation detector for analyzing radiation detected by the radiation detector and translating the detected radiation to an indication of the tissue glucose level.

The excited target is not glucose itself, but a molecular component of the patient such as, for example, a component of skin or other tissue, that is related, is sensitive to, or co-varies with glucose concentration, such as tryptophan, elastin, collagen or collagen cross links, NADH, or FAD. Suitable targets are structural components, and compounds and molecules that reflect alterations in the environment of matrix, cellular, or mitochondrial components, or any other cellular component reflective of metabolic activity, of the tissue and are sensitive to or correlate with tissue glucose concentration. The target may provide an emitted fluorescence signal that is related to the patient's blood glucose level, and/or absorb certain portions of the returned signal creating a unique signal correlatable with glucose concentration, or a combination of the two.

The radiation detector is responsive to the emission band of the target or species in the skin. Preferably, the excitation radiation is ultraviolet radiation or visible light, such as blue light. The radiation emitted at the tissue surface is preferably fluorescence radiation from the excitation of the non-glucose target.

The instrument may further include means for measuring scattering re-emitted or scattered radiation remitted from the irradiated skin and means for measuring absorbance, such as absorption from skin chromophores, like oxy- and/or deoxyhemoglobin, and melanin. The radiation emitted, reflected or transmitted from the excited target and signal therefrom correlates with the blood glucose of the patient.

Another embodiment of the invention is directed to a non-invasive analyte monitoring instrument comprising a radiation source for directing excitation radiation to a portion of a tissue surface, (i.e., about 0.5 to 4 square centimeters of skin), a radiation detector, and a processing circuit. Preferably, the analyte being "detected" maybe correlated with glucose. The radiation source is a visible light source or an ultraviolet light source that emits excitation radiation at least one wavelength that excites a target in the tissue.

The excited target emits radiation that correlates with the analyte level of the tissue or blood. The amount of fluorescence can reflect the quantity of a matrix, cellular or mitochondrial component that is related to the blood glucose level of the blood. The radiation from the excited target and received at the tissue surface may be affected by factors such as absorption, scattering, temperature, quenching, polarization, and remission of fluorescence. As with the previous embodiment, radiation received at the surface may be quenched or amplified by one or more matrix, cellular or mitochondrial components, or any other cellular component reflective of metabolic activity, in the tissue. The radiation detector is positioned to receive radiation emitted from the surface of the tissue. The radiation received at the surface of the tissue provides an indication of the analyte level of the patient. The processing circuit is operatively connected to the radiation detector and translates emitted radiation to a measurable signal to obtain an indication of the analyte concentration or trend in the change of concentration (collectively the analyte level).

Another embodiment is directed to a non-invasive method of detecting a glucose level of a tissue comprising: exciting a non-glucose target in the tissue wherein the target emits radiation such that the radiation received at the tissue surface is indicative of a glucose level of a patient; detecting radiation emitted by the target and transmitted through the intervening tissue to the surface; and determining the glucose level or trend in glucose levels from the radiation detected. In a preferred embodiment, the excitation radiation is ultraviolet or visible light.

Preferred targets for monitoring or detecting glucose are non-glucose molecular species in the skin such as tryptophan-containing proteins or a matrix target, like PDCCL (pepsin digestible collagen cross links) and non-pepsin digestible collagen cross links, elastin, or other matrix and non-matrix tissue components, such as cellular or mitochondrial, NADH, pentosidine, flavoproteins, FAD, and the like. Targets useful for detecting analytes are excited by ultraviolet or visible radiation and act as bioamplifiers or bioreporters. Targets may be structural matrix, cellular, mitochondrial, or other tissue components. Suitable targets reflect alterations within the environment of matrix and/or tissue components of the skin or other tissue with either creation of compounds that fluoresce or causing an extant compound to fluoresce and may act as bioamplifiers or bioreporters when excited with ultraviolet radiation. Alternately, quenchers, absorbers, or scatterers may be what are acting to amplify or report. Other targets may reflect changes in redox rates of analyte transport in the tissue.

Another embodiment is directed to a method for detecting diabetes in a patient comprising: exciting a non-glucose target using ultraviolet or visible radiation wherein the collection of light from the excited target is indicative of a glucose level or state of diabetes of a patient; detecting radiation emitted by the target; determining the glucose level from the radiation detected; and detecting diabetes based on the determined glucose level or other information.

Another embodiment is directed to an instrument for assessing changes in the structural matrix, cellular, or mitochondrial components, or any other cellular component reflective of metabolic activity, of the skin of a patient comprising means for measuring fluorescence emitted from the skin, means for measuring scattering, and means for measuring absorbance. This embodiment may further include means for irradiating the tissue with a plurality of wavelengths of excitation light and means for synchronously scanning the fluorescence emitted from the skin with the excitation light.

Another embodiment is directed to an instrument in which fluorescence measurements of matrix, cellular, or other components are reflective of the onset or state of diabetes.

Another embodiment is directed to a method in which fluorescence measurements of matrix, cellular, or other components is reflective of the onset or state of diabetes.

Another embodiment is directed to an instrument for assessing changes in the environment of the matrix, cellular, or mitochondrial components, or other cellular components reflective of metabolic activity, of the skin or other tissue of a patient comprising: means for measuring fluorescence; means for measuring scattering; and means for measuring absorbance. Preferred embodiments further include means for combining signals from the means for measuring scattering and means for measuring absorbance in visible, UV, or infrared regions with fluorescence measurements.

Still another aspect of the invention relates to a non-invasive method of assessing a change in the superficial structural matrix, cellular, or mitochondrial components, or any other cellular component reflective of metabolic activity, of a tissue, or a change in the environment of matrix, cellular, mitochondrial, or other components reflective of metabolic activity, comprising exposing the tissue to radiation at a first wavelength, detecting fluorescence emitted by exposed tissue, exposing the tissue to radiation of a second wavelength, detecting scattering re-emitted from the exposed tissue, and deriving an indication representative of the change in the structural matrix, cellular or mitochondrial components of the tissue, or a change in tissue matrix, cellular, or mitochondrial components, or other cellular components reflective of metabolic activity, or their environment, based on fluorescence, absorbance and scattering detected. The method may further comprise the step of detecting absorbance.

Another embodiment is directed to a non-invasive method for monitoring skin or tissue constituents in which information about or signature of a specific blood analyte level or disease process is provided comprising the steps of: exciting a target fluorophore; detecting radiation emitted by the fluorophore and transmitted through intervening tissue to the surface; and determining the information or signature from the radiation detected.

As will be clear to those of skill in the art, multiple excitation and emission wavelengths may be used in the various embodiments without departing from the spirit and scope of the invention. For example, multiple excitation wavelengths may be used while doing emission scans. Additionally or alternately, multiple emission wavelengths can be evaluated while doing excitation scans.

Other objects and advantages of the invention are set forth in part in the description which follows and, in part, will be obvious from this description, or may be learned from the practice of the invention.

DESCRIPTION OF THE INVENTION

Figure 1:
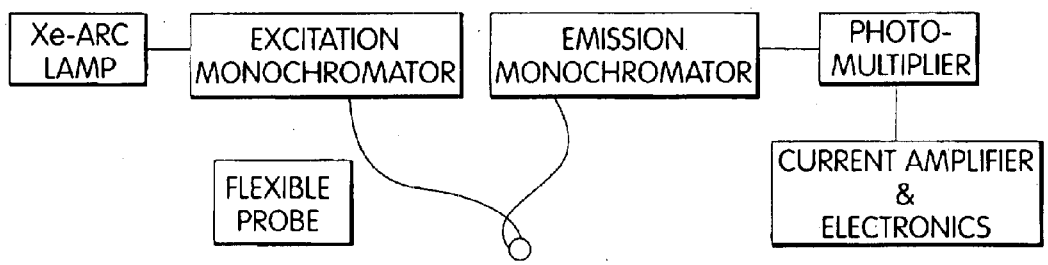
FIG. 1 A multipurpose skin spectrometer that provides data specifically relevant to signals correlating with blood glucose.

As embodied and broadly described herein, the present invention relates to devices and methods for quantitating, trending and/or reporting an analyte, such as blood glucose, to devices and methods for monitoring and regulating in vivo glucose levels, and to devices and methods for evaluating the structural matrix, cellular, or mitochondrial components, or other cellular components reflective of metabolic activity, of a tissue.

It has been discovered that by measuring fluorescence following irradiation of a tissue surface of a patient, such as the patient's skin, and by optionally assessing scattering and absorbance, the glucose level of a patient can be evaluated. It has been discovered that the fluorescence of a responsive target within the skin or the quantity of such a compound, which may be affected by components in the matrix, cellular, or mitochondrial, which influence the signal by amplification or quenching, is transiently affected by the radiation and can be correlated to the ambient glucose content. Potential explanations for the effect on fluorescence include: 1) an effect on observable quantum efficiency; 2) an effect on the number of fluorescent molecules present; 3) wavelength shifts in either excitation or emission space or both; or 4) quenching by some mechanism other than reduction of quantum efficiency (e.g., fluorescence lifetime changes, or some competing reaction scheme that has non-fluorescent species in it).

Long-term effects on collagen and other species has been previously observed with respect to diabetes (V. M. Monnier et al., Diabetes 37:867–872, 1988). However, a reversible component of this interaction that correlates with blood glucose levels and depends on the glucose level in the environment of collagen, preferably type IV collagen, and other targets has previously gone unnoticed. More specifically, although glucose itself does not fluoresce to any significant degree, when the blood glucose level of a patient changes, the observable quantum efficiency of fluorescence of a target such as, for example, pepsin-digestible collagen cross links (PDCCL), also changes other mechanism. Alternatively, in processes, e.g., metabolism, that have equilibria of fluorescent molecules that are influenced by glucose concentrations, the number of fluorescent molecules present in the tissues and thus the fluorescence of the tissue will change with the patient's glucose concentration. This change may be due, in part, to the direct and indirect effects of the relative presence of glucose or other molecules on the environment of target molecules and structures or the influence of glucose on equilibria of metabolic pathways containing fluorescent molecules. That presence may induce a reversible change in the observable quantum efficiency of fluorescence production by the target which can be detected and analyzed. Glucose molecules in the environment may be covalently or noncovalently coupled to the target (glycosylated collagen), free in the immediate vicinity of the target, or in the process of metabolism lead to the creation of new targets. For example, the number and characteristics of fluorescent molecules are created as part of metabolic process (e.g. NADH, FAD, flavoproteins, and the like).

Amount of fluorescent targets or characteristics of these targets may change in relation to glucose. Alternatively, the fluorescence of the target may remain constant and the effects of the environment or the intervening tissue may influence the signal recorded, or both the fluorescence of the target and intervening effects may change and produce data that can be seen to co-vary with blood glucose levels.

Targets may be in the dermal matrix, in the epidermal matrix, or in cells, mitochondria or the immediate vicinity of cells associated with the either the dermis or the epidermis. In this regard, the invention may also be used to directly assess the amount or degree of advanced glycation end products that exist in an area of the body such as, for example, in vessels, arteries or organs.

A fluorescent signal in the region of one demonstrated to originate from dermal collagen cross links has been identified, which signal slowly increases with aging and is also sensitive to transient exposure to ultraviolet radiation.

PDCCL fluoresces following excitation at 335–340 nm, with the emission maximum at 390 nm (N. Kollias et al., Journal of Investigative Dermatology, 111:776–81 1998). The fluorescent signal decreases monotonically with a single UV exposure, but recovers within hours. With multiple exposures, the effects appear cumulative, and recovery takes weeks. However, it has been discovered that transient changes in the recorded signal in the spectral region characteristic of these collagen cross links can be tightly correlated with blood glucose determinations.

It has been discovered that targets in the environment of matrix, cellular, or mitochondrial components, or other cellular components reflective of metabolic activity, such as collagen cross links, serve as bioamplifiers or bioreporters of ambient glucose concentrations and, thus, constitute a novel and sensitive means of non-invasively assessing glucose in real time. The method is also unhampered by absorption from competing species in the general area. In addition, there are only a few fluorophores, making signal analysis easier. Further, detector sensitivity is generally excellent and instrumentation and optical components, all of which are commercially available, are potentially simpler and less expensive than those used for infrared measurements.

It has also been found that skin fluorescence undergoes systematic changes with aging, and that in particular, the apparent intensity associated with tryptophan-containing proteins decreases, and that associated with collagen increases, as a function of age. These changes appear to be systematic. The present invention detects transient changes in fluorescence spectra that correlate with short-term changes in the concentration of blood analytes, and in particular to that of glucose. These short-term transient changes in fluorescence spectra are superimposed in the same spectral region on the long-term changes associated with aging.

It has been discovered that in vivo fluorescence spectra in the region 270–1,100 nm correlate with blood glucose levels. Experimentally, fluorescence spectra are measured non-invasively by placing a probe on the surface of the tissue in question, irradiating the tissue with excitation radiation, and measuring the radiation which has been re-emitted by fluorescent species (fluorophores) and transmitted back through the tissue to the tissue surface, where the probe captures it and transmits it for amplification and analysis.

Possible explanations for the changes in the observed spectra which correlate with glucose are divided into three broad categories: those in which one or more endogenous fluorophores alter their absorption or emission in some way, those in which new fluorophores are created, destroyed, or modified in a way that is correlated with blood glucose levels and those in which the output of the fluorophore remains constant, but the intervening medium (e.g., dermis, epidermis, and stratum corneum) changes its properties so as to affect radiation passing through it, to and from the fluorophore. The three categories are, of course, not mutually exclusive, so that mechanisms in all categories may be simultaneously present.

Explanations in the first category include (1) changes in the observable quantum efficiency of the fluorophore; (2) wavelength shifts of the fluorophore in either excitation or emission space or both; or (3) quenching by some mechanism other than reducing quantum efficiency (e.g., fluorescence lifetime changes, complexing, self-quenching, or some other competing mode of relaxation which does not fluoresce.)

Explanations in the second category include (1) creation of a new fluorophore, such as NADH from NAD; 2) degradation of an extant fluorophore, such as FAD from FADH; and 3) reflection of cellular or mitochondrial metabolism as ratios of fluorescent and non-fluorescent compounds.

Explanations in the third category include (1) alterations in the tissue scattering length and/or scattering isotropy, resulting in alteration of the emitted radiation reaching the surface of the tissue, or (2) changes in tissue absorption related to glucose, or (3) a combination of the previous two. For any of these, the fluorophore of interest (collagen, e.g., type V collagen, tryptophan, NADH, etc.) may be acting as an unchanging endogenous emitter, and apparent changes in the observed spectrum at the tissue surface are caused instead by the tissue scattering and absorption properties. Tissue absorption and scattering may affect the fluorescent signal, both by attenuating or altering the incoming excitation radiation and by attenuating or altering the outgoing fluorescent emission radiation. This attenuation or alteration may be wavelength dependent and can either increase or decrease the fluorescence emission detected.

Accordingly, one aspect of the present invention is related to a non-invasive in vivo glucose monitoring instrument that determines glucose concentration, changes in glucose concentration or trends in those changes (together collectively referred to as level), by measuring fluorescence of the skin following excitation of a target or species in the skin. Specifically, fluorescence signals obtained following irradiation of skin or other tissue can be correlated with glucose levels, or changes in glucose levels, by measuring fluorescence following excitation of targets or species within the environment of the matrix, cellular, or mitochondrial components, or other cellular components reflective of metabolic activity. Preferred targets are structural matrix, cellular, or mitochondrial components, or other cellular components reflective of metabolic activity, such as PDCCL. Another preferred target is epidermal tryptophan which, like other targets, may be bound to other compounds or structures, and intra cellularly or extracelluarly localized. Other useful matrix targets for excitation include collagenase-digestible cross links, elastin cross links, glycosaminoglycans, glycated collagen and glycosylated substances in a tissue. These targets may also be referred to as biosensors, as they are biological substances that detectably change in response to glucose content, or bioamplifiers, as they may amplify a signal indicative of systemic glucose levels. Another preferred target is NADH. The production of this molecule may reflect the metabolic state of the dermal or epidermal tissue, mitochondria, and/or cells.

A non-invasive glucose-monitoring instrument according to one aspect of the invention includes a radiation source capable of directing radiation to a portion of the surface of the skin (or other tissue) of a patient. The source emits radiation at least one wavelength that excites a target or species in the tissue whose fluorescence can be correlated with blood glucose content, such that the radiation received at the tissue surface provides a glucose level indication of the patient. In a preferred embodiment, the target is a molecule other than glucose, and is a structural matrix component, such as, collagen cross links. Alternatively, the target may be tryptophan. Another preferred target is NADH, FAD, Flavoproteins. When the target being detected is cross linked collagen, the ultraviolet radiation source is preferably operative to irradiate at approximately 330–345 nm, and the ultraviolet detector is sensitive to emitted wavelengths in the range of 370–410 nm, more preferably, 380–400 nm and, most preferably, 390 nm. As noted, another useful target whose change in emission may be detectable is tryptophan and preferably tryptophan-contain proteins. When the target being detected is tryptophan, the ultraviolet radiation source is preferably operative to irradiate at approximately 285–305 nm, more preferably at approximately 295 nm, and the ultraviolet detector is preferably sensitive to emitted wavelengths in the range of 315–420 nm, more preferably 340–360 nm, and most preferably, 345 nm. When the target being detected is NADH, the ultraviolet radiation source is preferably operative to irradiate at approximately 320–370 nm, more preferably at approximately 340 nm, and the ultraviolet detector is preferably sensitive to emitted wavelengths in the range of 400–550 nm, more preferably 450–470 nm, and most preferably, 460 nm. When the target being detected is FAD or other flavoproteins, the ultraviolet radiation source is preferably operative to irradiate at approximately 340–500 nm, more preferably at approximately 370–460 nm, and the ultraviolet detector is preferably sensitive to emitted wavelengths in the range of 500–600 nm, more preferably 520–560 nm, and most preferably, 530 nm. The radiation emitted by the target correlates with the glucose level of the patient. The spectral information can be converted into a number correlative to standard blood glucose determinations.

The instrument further comprises a radiation detector positioned to receive radiation emitted from an excited target at the tissue surface. The instrument may further include a processing circuit operatively connected to the radiation detector and operative to translate a level of emitted radiation into a measurable signal that is representative of, or may be correlated with, the blood glucose level. Alternately, the instrument comprises analyzing means operatively connected to the radiation detector for analyzing radiation detected by the radiation detector and translating the detected radiation to an indication of the tissue glucose level. The analyzing means preferably analyzes one or more parameters selected from the group consisting of wavelength of fluorescence, overall fluorescence, relative peak ratios, spectral shapes, peak shifts, band narrowing, band broadening and intensity. It may comprise means for applying one or more multi variate analysis methodologies selected from the group consisting of PLS, PCR, LDA, MLR, stepwise LR, wavelets and neural networks.

Preferably, the radiation source is ultraviolet light. Alternately, visible light may be used. The source may be a laser, diode or lamp. In a preferred embodiment, the radiation source may comprise a flexible-fiber optic arm or probe that directs the radiation to the target. In another embodiment, the light is directed onto the skin and collected through other optical means (e.g. lens). The probe may comprise a glass or quartz fiber and may be flexible and easily manipulated to examine a site anywhere on the patient's skin. The portion of skin irradiated may be between about 4 square cm or more but as little as about 0.2 square cm. However, the portion of skin irradiated may be as small as about 0.5 to 1 square cm or less. The radiation source may further comprise means for applying the source to the tissue surface at a constant pressure and temperature at the tissue surface. Preferably, the portion is a site which is most easily measurable on the patient such as on the arm or leg. Differences in pigmentation between different areas of the body as well as different patients can be factored or eliminated through selection of control input, and overcome.

In a preferred embodiment, the radiation source is configured to emit excitation radiation at a plurality of different wavelengths and the radiation detector is configured to synchronously scan radiation emitted by the target with the excitation radiation (e.g. an excitation-emission map, in which the excitation-emission pairs for fluorescence are represented in a three dimensional array with the X and Y axes representing excitation and emission wavelengths respectively with the Z axis corresponding to the fluorescence intensity returned at excitation wavelength X and emission wavelength Y). The radiation source may be an ultraviolet light or a visible light source.

Useful targets include structural matrix, cellular, or mitochondrial components, or other cellular components reflective of metabolic activity. For example, the target may be selected from the group consisting of a pepsin-digestible collagen cross link, a collagenase-digestible collagen cross link, a non-pepsin digestible collagen cross link, free tryptophan, tryptophan-containing proteins, elastin cross links, FAD, flavoproteins, NADH, other matrix, cellular or mitochondrial components, or combinations thereof.

In a preferred embodiment, the target is tryptophan and the radiation source is operative to emit radiation at between about 285 and 305 nm, or, more preferably, about 295 nm. The radiation detector is operative to detect radiation at between about 315 and 420 nm. In another preferred embodiment, the target is PDCCL and the radiation source is operative to emit radiation at between about 330 and 345 nm, or, more preferably, 335–340 nm. The radiation detector is operative to detect radiation at between about 370 and 410 nm. In another preferred embodiment, the target is NADH and the radiation source is operative to emit radiation at between 320 and 370 nm, or, more preferably, 340 nm. The radiation detector is operative to detect radiation at between about 420 and 520 nm. In another preferred embodiment, the target is FAD or other flavoproteins and the radiation source is operative to emit radiation at between 320 and 500 nm, or, more preferably, 370 nm and 460 nm. The radiation detector is operative to detect radiation at between about 500 and 560 nm.

The instrument may further comprise a display such as, for example, a visual, auditory or sensory display operatively connected to the processing circuit or analyzing means and operative to display the glucose level indication. The analyzing means may comprise means for monitoring a trend in glucose levels. In this embodiment, the instrument further comprises a device responsive to the analyzing means that is operative to administer a medication, such as insulin via an insulin pump, to a patient at a rate that corresponds to the glucose level indication or trend.

The instrument may include alarm means operationally coupled to the analyzing means that is activated when the glucose level indication exceeds a first predetermined value, falls below a second predetermined value or varies more than a predetermined amount (i.e., 20%) from a third predetermined value.

The instrument may also include a normalizing detector responsive to another target that provides normalizing information to the processing circuit to normalize the glucose level indication. Alternately, the instrument may have normalizing means which provides normalizing information to the analyzing means to normalize the glucose level indication. For example, the normalizing means may normalize for age, UV damage, skin color, temperature, hydration and pH.

The instrument may include means for measuring scattering. One such means comprises an illuminating means that emits radiation at an angle greater than 60 degrees to the target or, alternatively, illuminating means which emits radiation at between about 300 to 700 nm.

The instrument may further include means for measuring absorbance and the analyzing means may comprise means for adjusting the glucose level indication based on the scattering and absorbance measured.

Optionally, data may be analyzed and transmitted to a pump or other servo mechanism responsive to the processing circuit. The pump is incorporated into the system such that the pump administers insulin or other medication to the patient at a rate that corresponds to the glucose level signal. The pump may be internal or external to the body. It may be designed for long term management of diabetes or for acute regulation of glucose infusions for nutritional supplementation.

Referring to FIG. 1, an embodiment of the glucose monitor of the invention includes a Xenon arc (Xe-arc) lamp, double excitation and emission monochromators, a photo multiplier device, a simple current amplifier and a flexible probe. The probe may comprise fiber optic bundles which allow convenient evaluation of living systems. This embodiment can take the form of a multipurpose skin spectrometer or it may be modified to create a unit optimized to provide data specifically relevant to signals correlating with blood glucose. One advantage of utilizing fluorescent excitation spectra compared to fluorescence emission spectra is that the former are similar to absorption spectra, which aids in the separation and identification of the individual fluorophores in a complex spectrum. Although other components can be substituted for the elements in this embodiment, a Xe-arc or mercury lamp in combination with an excitation monochromator avoids the major constraint of laser sources, namely the limited number of excitation wavelengths.

Optionally, other types of sources, such as a diode laser, coupled with enhanced spectral analysis algorithms may be used. These algorithms may also incorporate variables such as skin coloration, type, age, exposure, temperature, skin hydration, pH, perfusion state, etc., all of which may be analyzed during testing. Hardware modifications and calibrations may be incorporated to take into account these and other variables. Specific algorithms and software may be embedded into a dedicated processor. For example, one design may comprise a night hypo/hyperglycemia monitoring instrument which is programmed to alarm by trending analysis parameters that correlate with significant changes in blood glucose. Alternatively, monitoring could be performed with a transportable fiber-based fluorescence spectrophotometer with double monochromators, both on the excitation and emission paths. This allows the evaluation of different subsets of collagen cross links and tryptophan signals and other fluorophores present (NADH, FAD, flavoprotein) as well as allowing the estimation of epidermal melanin pigmentation or other tissue pigments. Optimized instruments (e.g. Fluorolog) may duplicate and incorporate the functionality and data processing requirements incorporated from appropriate studies.

Another embodiment uses a fiber-based fluorescence spectrometer with two double monochromators and a high intensity excitation light source (i.e. 350 W Xe-arc). The double monochromator design minimizes stray light, which tends to be high because of the high level of light scattering by the tissues. The probe is a fiber optic device that allows collection of data from different skin sites on the body. Probe design is optimized to permit ease of use and reproducibility. Optimization of light sources, filters and software can be designed to perform multiple scans that maximize the collagen fluorescence signals. In one embodiment, three scans are performed. This provides information on PDCCL (340/390 nm), the collagenase digestible collagen cross links (370/460 nm) and the collagen/elastin cross links (420/500 nm), NADH (340/460 nm), FAD (370 and 460/530 nm), among other species. The system may also provide data on tryptophan, an epidermal fluorophore having an excitation wavelength of 290–315 nm and an emission wavelength of 340–400 nm, among other species. Additional scan types include emissions scans and synchronous scans, and excitation-emission maps.

Devices may be small and lightweight desktop units useful in health care provider or home settings. A remote probe may be connected to the system through a flexible fiber optic bundle. Data output may consist of a reporting of a quantitative number that correlates with blood glucose readings, along with spectral data, which may be displayed on a separate small I/O terminal or laptop computer. The software further contains diagnostic overlay capabilities.

As will be clear to those of skill in the art, multiple excitation and emission wavelengths may be used without departing from the spirit and scope of the invention. For example, multiple excitation wavelengths may be used while doing emission scans. Additionally or alternately, multiple emission wavelengths can be evaluated while doing excitation scans. In one such preferred embodiment, 260 to 510 nanometers are utilized in a synchronous 50 (sync50) scan.

Another device allows monitoring of glucose levels by providing spectral information reflective of glucose levels on a continuous or repetitive basis. Analysis may be enhanced by comparing with temporally proximal and distal data points. In one embodiment, this would be used throughout the night with a built-in alarm, to alert the patient to abnormal decreases or increases in glucose levels. The unit, which may be the size of a clock radio, may have a fiber optic cable to connect to the patient, similar to existing apnea monitors and pulse oxymeters. Another portable device may be placed in contact with the skin for periodic momentary glucose readings. It may have an LCD readout for glucose levels or an auditory reporting capacity, or both, as well as memory to store several hundred glucose readings and a data output to download stored data. The device may alternately have a sensor unit directly attached to the patient that is coupled to an analyzer or alert system via RF communication, thereby obviating the need for direct physical connection by cable/fiber/wire between the patient and the unit.

An alarm may be operationally coupled to the processing circuit or analyzing means such that the alarm is activated when the glucose level indication exceeds a first predetermined value (such as 200 mg/dL), falls below a second predetermined value (such as 70 mg/dL), or varies more than 20% or any desired amount from a third predetermined value (such as the previously measured level or a baseline level determined for the patient). Alternately, the alarm may be triggered in response to a more complex algorithmic analysis of data or based on evaluation by trending analysis over time.

The instrument may further comprise a normalizing detector responsive to another target in the tissue, such that the processing circuit or analyzing means is responsive to the normalizing detector to normalize the glucose level indication. For example, a current or latest glucose level signal may be normalized by comparing it to a previously determined glucose level signal which has been calibrated by comparing it directly with a conventionally determined blood glucose level. Alternatively, normalization may involve comparison of emissions from the same target but at another wavelength, comparison of emissions from a non-target or another structural or circulating component of the body, or simply taking a reading from another skin site. Normalization may also be performed by comparison to similar data from another point or points in time taken from the same individual, or utilizing a stored database or spectral library. Normalizing may alternately comprise obtaining a baseline signal before any prolonged activity where continual measurements would be difficult such as, for example, before driving or sleeping, and watching for changes or trends of changes. The previously determined glucose level signal may also be compared with a level assessed from a simultaneously drawn blood sample. In addition, scattering evaluation and absorption, such as by skin chromophores, may be factored into the normalizing process.

The instrument may optionally comprise means for measuring scattering re-emitted from the tissue. As discussed below, the means for measuring scattering may comprise a skin illuminating means that emits radiation at an angle greater than 60 degrees to the target or it may comprise a skin or tissue illuminating means which emits radiation at between about 280 to 700 nm. Re-emitted radiation is then collected and analyzed.

Generally, longer wavelengths penetrate down into dermis. The use of a 60 degree angle of illumination to the skin surface separates the diffuse from the spectral reflectance as there is essentially no spectral reflectance with the fibers placed on the skin.

The instrument may include a portable housing in which the radiation source, the radiation detector and the processing circuit are disposed. The instrument may include a battery compartment disposed in the housing and a pair of battery contacts operatively connected to the ultraviolet radiation source, the ultraviolet radiation detector, and the processor. Data can be electronically recorded, stored or downloaded for later review or analysis. The instrument may further comprise attachment means for attaching the radiation source, a portion of, or all of the device to the patient. The portable housing, the ultraviolet radiation source, the ultraviolet radiation detector, and the processor may be designed so that they weigh in combination less than 3 kg, more preferably less than 1 kg, and most preferably, less than 0.5 kg. The instrument may optionally include an attachment mechanism for attaching the housing to the patient. Alternately, the instrument can be miniaturized; in such an embodiment, a microprocessor is incorporated onto a dermal patch, which may be operatively connected to other devices that provide input directly to a pump or other biodelivery system, such as a trans mucosal or inhalational system, which may deliver insulin, glucose-containing solutions or other appropriate medication to the patient.

The instrument may also be constructed using small components composed of inexpensive, possibly recyclable materials such as plastics and paper, so that the entire instrument or a significant portion is disposable. For example, the entire device can be incorporated into a patch worn anywhere on the body and secured with adhesive tape, hook-and-loop fastener or another suitable means. After expiration or depletion of an integral battery, the patch can be safely and easily disposed of and a new patch secured. Such instruments weigh less than 1 kg, preferably less than 0.5 kg and more preferably less than 0.1 kg.

The processing circuit or analyzing means is preferably operative to translate the level of detected radiation into a measurable glucose level signal that is indicative of the glucose level in the tissue. The signal may be directly evaluated, or it may be compared to stored reference profiles, to provide an indication of changes from previous levels or trends in the patient's glucose level. Although a preferred embodiment measures radiation or fluorescence following irradiation of the skin, the present invention can also be used to assess glucose levels by evaluation of other tissues. For instance, glucose levels may be assessed in accordance with the present invention by detecting radiation or fluorescence following irradiation of the surface of other tissues, such as mucous membranes, or irradiation of the mucosa, submucosa or serosa of any organ.

One embodiment of the invention is directed to a non-invasive analyte monitoring instrument comprising a radiation source for directing excitation radiation to a portion of a tissue surface, such as skin, a radiation detector, and a processing circuit. Preferably, the analyte being detected is glucose. The radiation source is a visible light source or an ultraviolet light source that emits excitation radiation at least one wavelength that excites a target in the tissue.

The excited target emits radiation that correlates with the analyte level of the tissue. The radiation from the excited target received at the surface may be affected by factors such as absorption of emissions and scattering. For example, radiation received at the surface may be quenched or amplified by one or more matrix, cellular, or mitochondrial components, or any other cellular component reflective of metabolic activity, in the tissue. The radiation detector is positioned to receive radiation emitted from the surface of the tissue. The radiation received at the surface of the tissue provides an analyte level indication of the patient. The processing circuit is operatively connected to the radiation detector and translates emitted radiation to a measurable signal to obtain the analyte level indication.

Another aspect of the invention relates to a non-invasive method of detecting a glucose concentration or level in a tissue or body in vivo comprising the steps of: exciting a non-glucose target in the tissue causing the excited target to emit radiation such that the radiation received at a tissue surface is indicative of a glucose level of a patient; detecting radiation emitted by the target and transmitted through the intervening tissue to the surface; and determining the glucose level or trend in glucose levels from the radiation detected. In a preferred embodiment, the excitation radiation is ultraviolet or visible light. Depending on the desired target, the excitation radiation may have a wavelength of about 280–650 nm. The radiation emitted by the target is fluorescent radiation.

Alternately, or in addition to detecting fluorescence intensity, other variations in fluorescence may be evaluated to assess glucose levels, such as variations in the overall fluorescence. This includes, but is not limited to, variations in relative peak ratios, spectral shapes, peak shifts, band narrowing and broadening, etc.

Preferably, the target is a matrix target such as collagen cross links, a cellular component (e.g. an intracellular tryptophan-containing protein), or a mitochondrial component such as mitochondrial NADH. The method may optionally include the step of determining whether to take steps to adjust the patient's glucose level in response to the derived or determined glucose level, followed by the step of administering insulin or another pharmaceutical composition in response thereto. For example, glucose or insulin administration may be adjusted in order to adjust the patient's glucose level. The method may include any one or more of the steps of reporting the information to the patient, determining whether to take steps to adjust the glucose level, recommending a dosage, or administering the composition, such as insulin, to the patient in response to the indication derived. Alternately, the method may comprise the step of adjusting the glucose level of the patient in response to the glucose level or trend determined. This may be accomplished by administering insulin or another medication to the patient, by using a syringe, a pump or another suitable biodelivery system, mechanical or chemical, which may be implanted or external to the body. The method may also include the step of displaying a glucose level indication related to the indication derived or providing a warning to the patient. The method may further include the step of normalizing the glucose level determined, such as by normalizing for one or more variables selected from the group consisting of temperature, perfusion state, age, UV damage, skin color temperature, hydration and pH.

The steps of exciting, detecting, and determining may be performed continuously or at any appropriate interval, for example, by the minute, hourly, daily or every other day for the same patient and over a period of days, weeks, months or years.

Optionally, the method may include actuating an alarm in response to the glucose level when the glucose level exceeds a predetermined first level, falls below a predetermined second level or varies more than a set percentage, such as for example, 10%, 20%, 30%, 50% or 100% or more from a predetermined third level, or changes in such a way that meets criteria of a specifically designed algorithm. The method may further comprise the step of measuring scattering re-emitted from the skin or irradiated tissue surface and utilizing the resulting data to initiate or assist in actuating a process aimed at adjusting the glucose level accordingly.

In this method, the step of determining the glucose level may comprise analyzing the radiation detected using one or more multi variate analysis methodologies selected from the group consisting of PLS, PCR, LDA, MLR and stepwise LR.

The step of exciting may comprise irradiating a target with excitation radiation at a plurality of wavelengths and the step of detecting radiation may comprise the step of synchronously scanning the emitted radiation and excitation radiation or the acquisition of an excitation-emission map.

The step of excitation may comprise application of a probe incorporating a radiation source to the skin. The probe may be applied to the skin at a constant pressure or temperature. The position of the probe on the skin may be varied during detecting.

Another embodiment of the invention is directed to a method for detecting diabetes in a patient comprising: exciting a non-glucose target using ultraviolet or visible radiation, such that the collection of light from the excited target is indicative of a glucose level of a patient or state of diabetes; detecting radiation emitted by the target; determining the glucose level or state of diabetes from the radiation detected; and detecting diabetes based on the determined glucose level provided by the collection of light from the excited target.

Instruments and methods of the invention are advantageous in that they provide information relative to blood glucose and permit glucose levels to be evaluated non invasively. Such non-invasive instruments allow people with diabetes to monitor glucose levels without the pain, inconvenience, and risk of infection associated with obtaining a blood sample. By making monitoring safer and more convenient, people with diabetes can monitor their glucose levels more frequently and therefore control levels more closely. Safer and more convenient glucose level monitoring reduces the likelihood of measurements being skipped.

Furthermore, by coupling instruments according to the invention with a pump or other device which can deliver insulin or another therapeutic agent to the patient, or using a transmitter or other suitable communication device, such that the pump or device is responsive to the glucose signal, even finer automatic glucose level monitoring may be achievable. For example, the transmitter may remotely transmit the signal to a pump, such as a servo pump, having a receiver responsive to the transmitted signal. The pump is preferably responsive to information derived from or analysis of the spectral signal. The pump may then provide insulin or other appropriate medication to the patient. Alternately, or in addition, the information may be sent to a remote monitor.

As will be clear to those of skill in the art, the instruments and methods of the present invention can also be used in forensic applications, to allow the non-invasive and non-destructive assessment of forensic tissues. In addition, the instruments and methods may be used to detect and diagnose diabetes, monitor the progression of diabetes, and detect and monitor other disorders involving hyper or hypoglycemia or abnormal blood sugar metabolism. Although the term in vivo is used to refer to living material, it is intended herein to encompass forensic applications as well.

Figure 2:
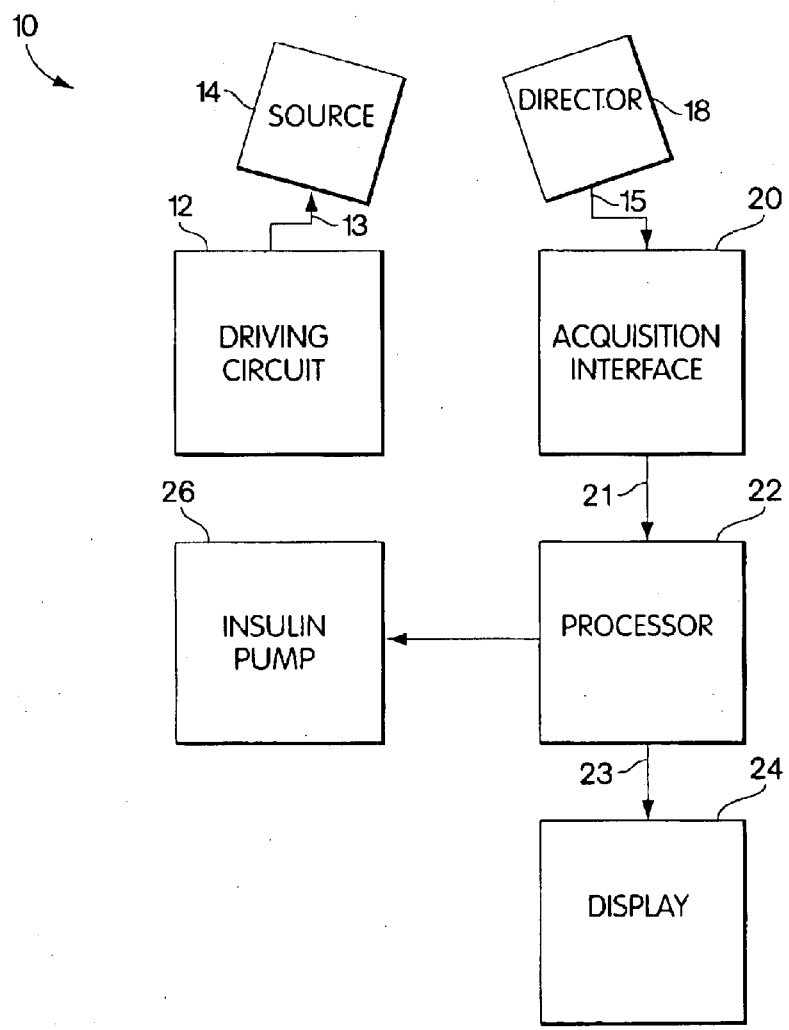
FIG. 2 Block diagram of one embodiment of a glucose level monitoring instrument.

Another embodiment of the present invention is depicted in FIG. 2, which depicts a glucose level monitoring instrument 10 including source driving circuit 12 having an output provided to an input 13 of a source 14. Source driving circuit 12 controls the illumination, provided by source 14. Source driving circuit 12 may take a number of forms, depending on the nature of the source and the acquisition. Examples include a regulated power supply or a pulsed modulator.

Source 14 preferably comprises an ultraviolet light source, such as a continuous mercury lamp, a pulsed or continuous xenon flash lamp, or a suitable laser. Useful lasers include, but are not limited to, nitrogen lasers, doubled OPO (tunable laser) and tripled Nd YAG pump devices. Useful pulsed sources include a 2-channel lock-in amplifier or a gated CCD. The output of source 14 may be filtered to restrict illumination to within excitation bands of interest. Its intensity (and pulse width if applicable) is preferably set at a level that minimizes exposure while optimizing signal-to-noise considerations. It is also possible to irradiate the sample with two or more short (e.g., femptosecond) pulses of multi photon light having a wavelength two or more times longer than the wavelength of interest, such that the radiation penetrates to a different degree or depth. The source is positioned to illuminate an area of interest on the patient's skin 16.

Glucose level monitoring instrument 10 also includes a detector 18 that is sensitive to ultraviolet and visible light emitted by the species that is excited by the source 14. The detector has an output 15 operatively connected to an input of an acquisition interface 20, which may be an analog-to-digital converter with an analog input operatively connected to the detector output. A digital output port 21 of the acquisition interface is operatively connected to processor 22.

Processor 22 is operative to convert the digital detector output signal into a glucose level signal. The processor may perform this conversion by applying various signal processing operations to the signal, by comparing signal data with stored reference profiles, or by other appropriate methods. It has an output 23 provided to a display 24, permitting the glucose level indication to be presented to the user. The output may be directly provided to display 24, or sent remotely via a transmitter. Display 24 may be an alphanumeric display which displays the glucose concentration as a percentage.

The glucose level monitor instrument 10 may also include a medication delivery device, such as insulin pump 26, which is responsive to the glucose level signal or other spectroscopic data or analysis provided by processor 22. A transmitter may be used to transmit the glucose level signal of processor 22 to the pump. The pump is configured so that it converts the glucose level signal received from processor 22 into an insulin dispensing rate. A single bolus of insulin may also be administered based on the glucose level signal. The use of an insulin pump allows the glucose level or trend to be controlled both continuously and automatically. The medication delivery device can also deliver another therapeutic substance, or administer an electrical, chemical, or mechanical stimulus. Miniaturized devices may be constructed of disposable materials such as plastics and paper to further reduce cost. Instrument 10 may be implemented in a number of different ways. It may be implemented at a board level, with the various elements described being separate components, mounted on a circuit board. Many of the elements may also be integrated into a dedicated special-purpose integrated circuit allowing a more compact and inexpensive implementation. Alternatively, the components may be miniaturized further to create an implantable device or a dermal patch. In integrating and miniaturizing the various functions of the instrument, many of them may be combined. Important algorithms may be embedded.

Instrument 10 may also include a normalizing section. The normalizing section is designed to reduce or eliminate the effect of variations, such as the intensity of source 14 or skin heterogeneity or day to day variations in the patient's tissue. A normalizing section may include a second detector that is responsive to a species in the skin that fluoresces but does not respond to glucose concentration. It may also normalize to a signal collected at another time, another site, or another wavelength or from a different internal or external target. Processor 22 may receive signals from the two detectors and derive a normalized glucose level signal. Preferably instrument 10 includes a portable housing bearing ultraviolet radiation source 14, ultraviolet radiation detector 18, acquisition interface 20 and processor 22. Instrument 10 may be powered via battery contacts by a battery contained in the battery compartment located within the housing. Preferably, the entire assembly weighs in combination less than 20 kg, preferably less than 10 kg and more preferably less than 1 kg. Highly portable embodiments which weigh under 1 kg may be attached to the patient in a monitoring position, such as by an elastic or hook-and-loop fastener strap.

The instrument may further include a system response detector similar to correction system, which allows system response to be checked daily.

In operation, a physician or the patient places source 14 close to an area of interest on the patient's skin 16. Preferably, this area is one that is not regularly exposed to sunlight, such as the inside of the upper arm. The physician or patient may then start the instrument's monitoring sequence. The monitoring sequence begins with driving circuit 12 producing a driving signal that causes source 14 to irradiate the area of interest on the surface of the skin 16 with one or more bands of ultraviolet radiation. The spectral content of this radiation is selected to cause one or more targets within the skin to fluoresce. These targets may include tryptophan, tryptophan-containing proteins, collagen cross links, NADH, flavoproteins, or other suitable targets. The excitation/emission wavelengths for tryptophan-containing proteins, collagen cross links, NADH and flavoproteins are 295/340–360 nm, 335–340/380–400 nm, 340/460 nm, and 370 and 460/530 nm, respectively. To increase the sensitivity of the measurement, it is also possible to pre-expose the area of interest with a higher intensity of radiation to quench the site before making measurements. Note also that the excitation and emission wavelengths are representative of the molecular species targeted. Under circumstances where the target is responsive to multiple different wavelengths and provides different information from each, or where targets and non-targets are responsive to the same wavelength, more accurate and qualitative values may be obtained by identifying and eliminating background and other interfering data.

The target absorbs the radiation from the source and emits it back to detector 18. More specifically, fluorescence is emitted from the target molecule and/or light is scattered by the target then remitted. Detector 18 derives a signal representative of the received emitted radiation and provides it to the acquisition interface 20. Acquisition interface 20 translates the derived signal into a digital value, which it provides to processor 22. Processor 22 converts the digital value into a display signal, which it provides to display 24. The display signal may take the form of an alphanumeric representation which correlates with the concentration of glucose in the blood, or it may include another kind of display signal to be used with another type of display. For example, it is possible to use a color coding scheme to indicate levels of glucose, or indicate dosage amounts to the patient on the display based on the signal received at the detector. The display need not be a visual display; tactile actuators, speakers, or other machine-human interfaces may be employed. The glucose level signal produced by the processor may be directly displayed to indicate the patient's glucose level. Alternately, the processor may first compare the data from the detector with stored reference profiles, such as the patient's prior levels, to provide information regarding trends in the patient's glucose level.

Still another aspect of the invention is related to a glucose monitoring system with alarm features. Parents of children with diabetes are under a continuous threat that a severe hyper- or hypoglycemic event may occur without their knowledge, such as during the night, with potentially fatal consequences. There are an increasing number of individuals with diabetes in need of a device for monitoring their glucose levels, including trends in their glucose levels. Accordingly, this aspect of the invention is related to a monitoring device with an alarm that alerts a parent or other interested person in the event of large or dangerous changes or trends in the blood glucose levels of a patient. The device reports systemic hyperglycemic and/or hypoglycemic events using fluorescent detection of alterations in the environment of matrix, cellular, or mitochondrial components, or other cellular components reflective of metabolic activity, that reflect changes in blood glucose. Alternately, the device may detect the change in fluorescence from the excitation of another suitable species, such as tryptophan, or changes in quenching. The device may be completely portable, miniaturized and/or disposable allowing its use in nearly any environment.

The alarm may be any suitable alarm including, but not limited to, a sound alarm or a radio transmitter that activates a sound or light emitting unit in the proximity of the parents or other interested person. The alarm may be audible, visible, vibrating or any other sensory detectable type. For example, in one embodiment, the patient's glucose level is measured once or at a plurality of intervals shortly before the patient goes to sleep to determine a baseline glucose level. The device is programmed to take measurements of the patient's glucose level at periodic intervals during the night, and to then compare these results with the baseline. If the glucose level varies more than a predetermined percentage from the baseline either simply or utilizing specifically designed algorithms, an alarm sounds. Although any desired percentage variation can be selected, in a preferred embodiment, the alarm is activated when the glucose level varies more than 5%, 10%, 20% or more from the previously determined baseline or in accordance with a previously defined set of parameters or specifically designed algorithms. Alternately, or in addition, the alarm is triggered if the patient's blood glucose level exceeds a first predetermined level (i.e., it exceeds 200 mg/dL) or if it falls below a second predetermined level (i.e., it falls below 70 mg/dL). When the alarm sounds, the patient can then be administered insulin (or other suitable medication) if the glucose level is too high, or can be given a source of sugar if the glucose level is too low. Alternatively, or in addition, the alarm may be triggered if other analysis or trending patterns occur or if the rate of change exceeds a predetermined amount.

Optionally, the processor of this device, or the processors or analyzing means of any of the monitoring devices disclosed herein, may include means for storing and displaying a plurality of sequential measurements, so that trends which occur during the night or during other time periods of interest may be saved and evaluated. The measurements can be taken continuously or repetitively at predetermined intervals. For example, a patient can be periodically monitored after the administration of one or more of the various forms or sources of insulin (i.e., lente, ultralente, semilente, regular, humalog, NPH etc.) or other glucose regulatory therapies to determine or help to determine the most suitable treatment protocol for the patient. This may be influenced by a comparison to other readings over time, a broader data base, a derivation based on the slope of the change of the signal over time and where on the scale of patient risk a particular assigned glucose might fall.

As mentioned above, the fluorescence signals measured from the excitation of PDCCL and other tissue components are affected by the changes in the scattering properties of the superficial structural matrix. As the electrolyte balance in the micro environment of collagen cross links changes, changes are induced in fluorescence. Changes in fluorescence also can occur with modification of metabolic components or from alterations in the equilibria of fluorescent metabolic compounds. In addition, the change in electrolytes also produces a change in the local index of refraction and thus a change in the scattering properties. The change in scattering causes a change in the fluorescence. Specifically, scattering will change the detectable or measurable fluorescence by altering the intensity of the exciting light or diminishing the emitted fluorescence. It may also alter the effective sampling volume, but it does not directly affect the fluorescence. The matrix scatters light independent of the local refractive index. These are two separate events. Correction can be made for changes in the measured fluorescence induced by scattering.

Figure 10A:
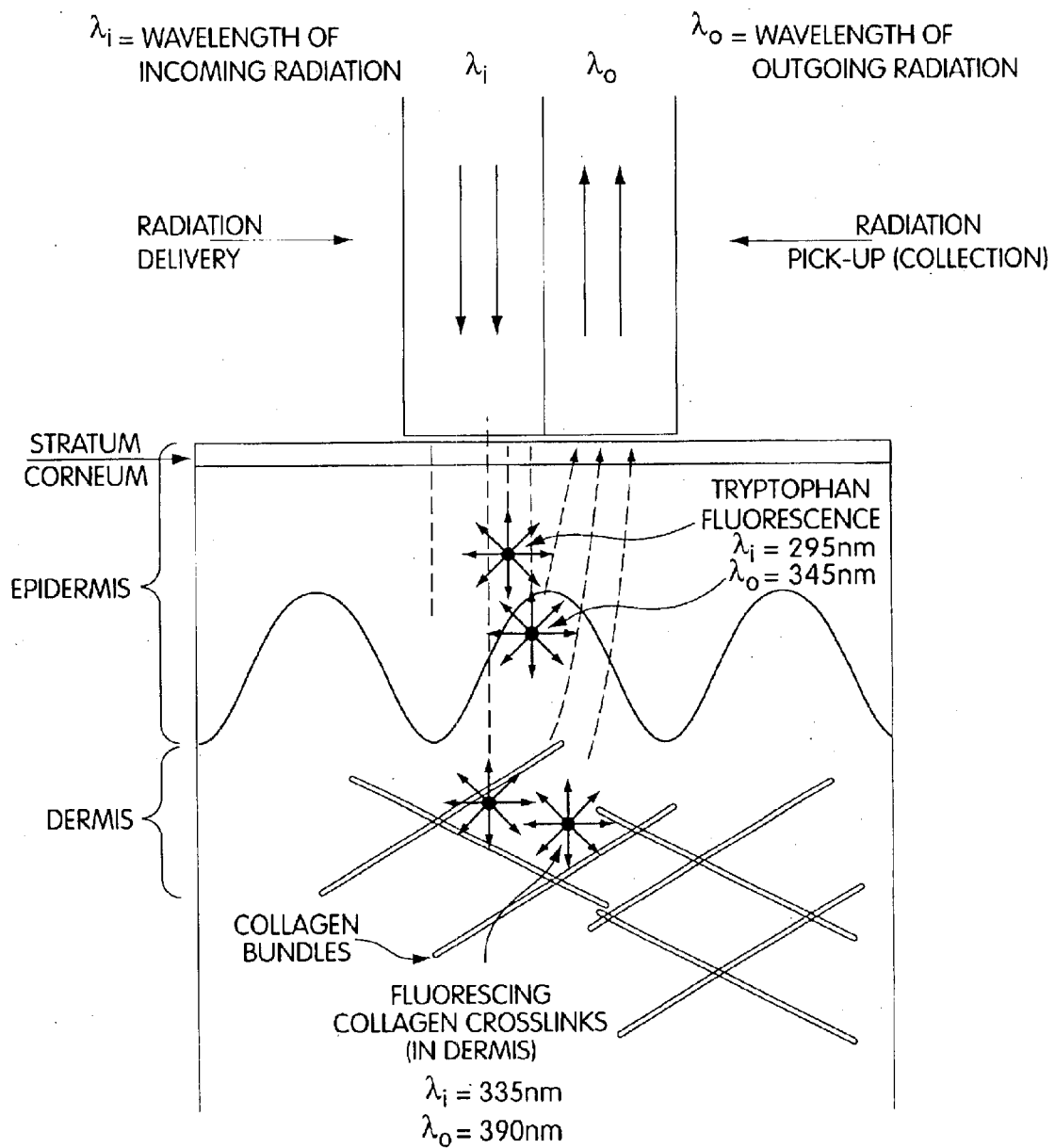
FIG. 10A A diagram depicting collection of fluorescence spectra with components attributable to tryptophan-containing proteins and collagen cross links following irradiation with UV light.

A diagram depicting fluorescence of two species sensitive to glucose concentration following irradiation of the skin is depicted in FIG. 10A. Incoming radiation at wavelength $\lambda i$ is directed towards the skin. It penetrates the stratum corneum. If $\lambda i$ is 295 nm, fluorescent radiation ($\lambda o$) will be emitted at 345 nm by tryptophan in the epidermis of the skin. If $\lambda i$ is 335 nm, fluorescent radiation will be emitted ($\lambda o$) at 390 nm by the collagen cross links in the dermis.

Figure 10B:
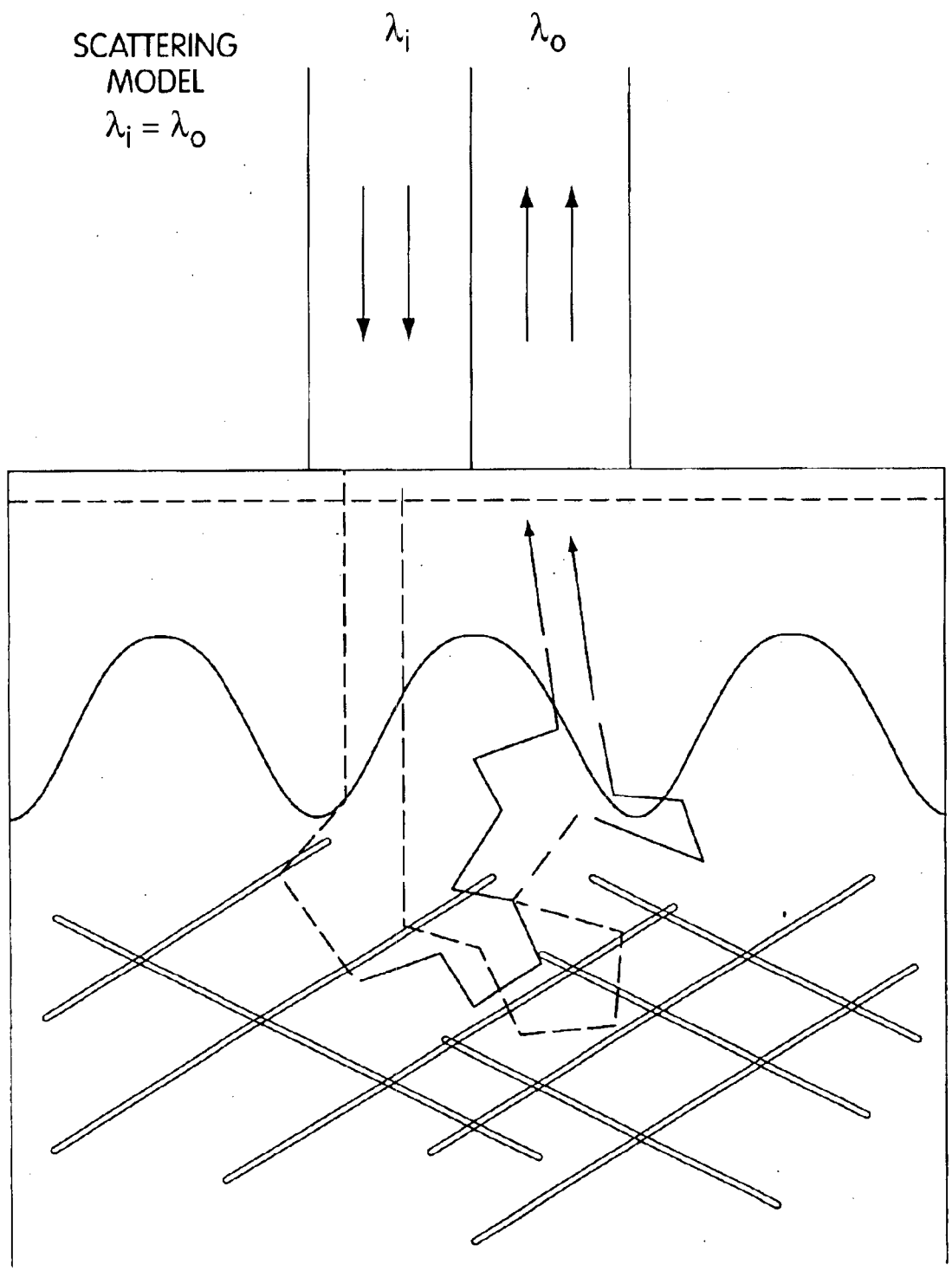
FIG. 10B A diagram depicting scattering according to a scattering model.

A diagram depicting a scattering according to a scattering model is depicted in FIG. 10B which shows collagen cross links in the dermis bending incoming light ($\lambda i$) in different directions. There emitted light ($\lambda o$) is at the same wavelength as the incoming light ($\lambda i$), but is scattered due to changes in the local index of refraction. By independently measuring scattering in the matrix, the monitoring of blood glucose levels by measuring fluorescence, as described above, can be enhanced. Specifically, the results from the assessment of scattering can be used to correct for changes in fluorescence induced by changes in the scattering properties of the relevant layers of the dermal matrix.

Accordingly, another aspect of the invention is related to a device that measures the scattering properties of a target such as superficial collagen dermal matrix in the skin, which is affected by changes in the chemical environment which can be correlated with blood glucose levels. Although it has been previously reported that the scattering properties of the skin (dermal matrix) change with glucose concentration and that these changes are measurable with photon migration techniques in the near infrared (NIR), the use of NIR wavelengths provides a sample of the whole dermis and subcutis (does not measure one signal specific for glucose, but rather many signals that are neither specific for glucose nor reliably linked to glucose levels in a linear fashion). In contrast, the present invention assesses the scattering properties of the dermis, as opposed to the deeper layers. Such scattering of polarized light by the dermal matrix is most noticeable in the range 380–700 nm.

Assessment of scattering in tissue, such as the dermis, associated with changes in blood glucose can most preferably be measured by using short wavelengths (330–420 nm) or launching the illuminating light at large angles (preferably>60°). Short wavelengths are preferably used because they penetrate to a small depth into the dermis. Alternately, changes in scattering induced by the presence of glucose may be measured using light in the visible range of 620–700 nm and looking for changes in signal intensity.

One of the benefits of assessing scattering of the superficial dermis, as opposed to deeper layers of the dermis, is that fluorescent signals from PDCCL's and other matrix, cellular, or mitochondrial components, or other cellular components reflective of metabolic activity, originate there and are affected by the changes in the scattering properties. Further, the superficial layers of the dermis (in areas of the body receiving minimal environmental insults) are well organized and this would be reflected in scattering of polarized light. Since glucose has a strong polarization rotation property, such changes may be measurable when monitoring at a submillimeter resolution, but when monitoring on a gross scale the effects of local organization would be canceled out. Increases in fluorescence may be compensated for by decreases in the effective scattering, making the fluorescence signal difficult to separate from background noise. By independent measurement of the scattering with non-polarized and with linearly polarized light, fluorescence detection may be enhanced, allowing it to stand on its own merit as a method of indirect measurement of glucose concentration.

Figure 11:
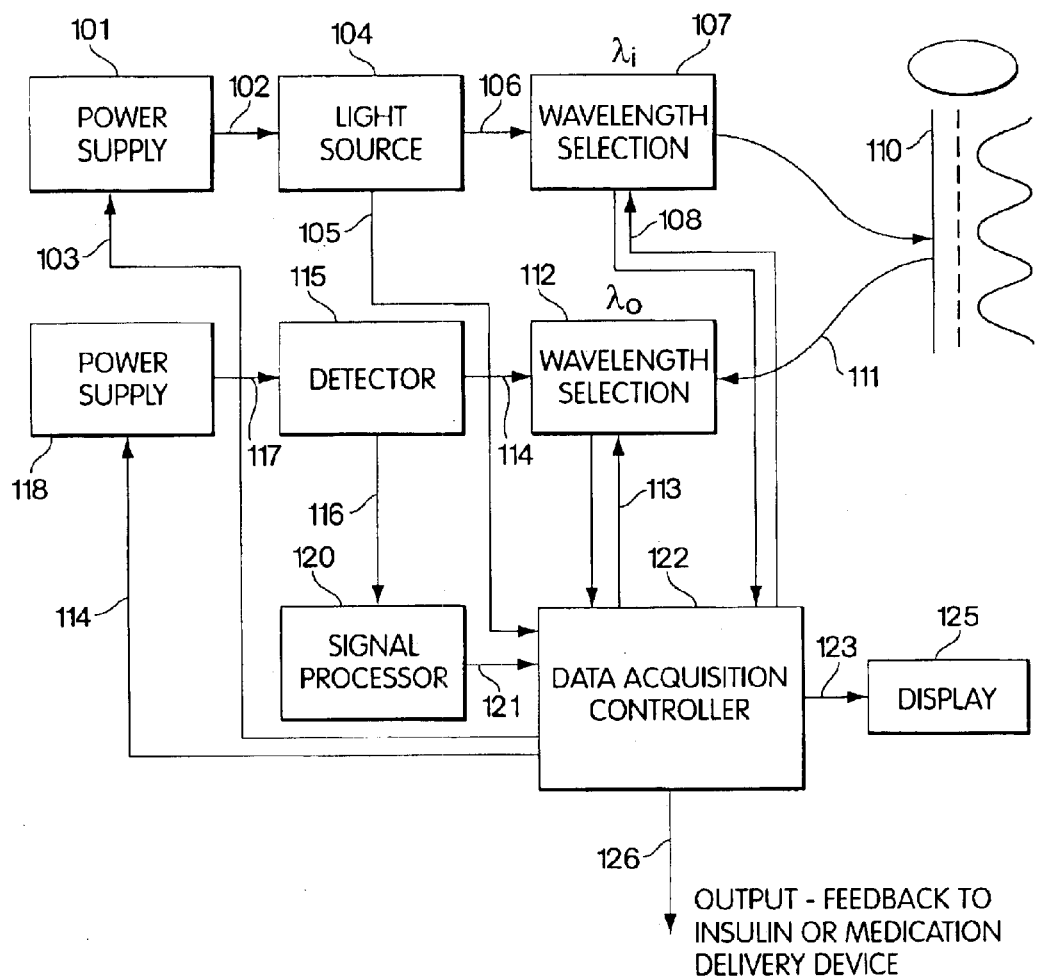
FIG. 11 Block diagram of a monitoring instrument that can be used to monitor tissue glucose levels or evaluate changes in the structural, or the environment of, matrix, cellular, or mitochondrial components, or other cellular components reflective of metabolic activity, of a tissue.

FIG. 11 depicts an embodiment in which both fluorescence of the superficial dermis and scattering are evaluated in order to assess glucose levels. Although this embodiment is described in connection with monitoring blood glucose, as will be clear to those of skill in the art, it can be adapted to assess the status of other analytes, or to detect changes in the superficial structural matrix or matrix, cellular, or mitochondrial components, or other cellular components reflective of metabolic activity, of a tissue. Instrument 100 comprises a power supply 101 connected via connection 102 to a light source 104. Light source 104 may be a lamp, an arc lamp, a laser, or other suitable illumination device. Power supply 101 receives feedback 103 from data acquisition controller 122 to regulate the intensity, synchronization or pulse rate of the light emitted from light source 104. Light source monitor output 105, which may comprise a PIN diode, Avalanche diode, photo multiplier, CCD or other suitable device, couples the light source 104 to data acquisition controller 122. Light 106 is directed to wavelength selection device 107, where an appropriate wavelength is selected, and selected light wavelength output 109 is directed via a fiber, prism or a combination, or directly through the air, to illuminate skin 110. Wavelength selection device 107 may comprise a monochromator, a filter or a combination of both. If a laser source is used as light source 104, a filter or other wavelength selection device may not be needed. Wavelength selection device 107 is coupled via signal connection 108 to data acquisition controller 122 to enable selection of the wavelength and to verify the present wavelength.

Fluorescent signals are emitted and scattered light is re-emitted from skin 110. The fluorescent light and reflective intensity 111 is picked up by wavelength selective device 112, which may comprise a monochromator, filter or a combination. Wavelength selective device 112 provides a light output 114 to detector 115. Detector 115 may comprise a photo multiplier, diode, Avalanche diode, CCD or other suitable detection device. The signal from detector 115 is transmitted to signal conditioner/processor 120 via signal connector 116. Detector 115 is supplied power via power cable connection 117 from power supply 118. Data acquisition controller 122 provides input to power supply 118 via signal connection 119 to allow selection of sensitivity or synchronization with the light source. Wavelength selection device 112 is coupled via connection 113 to data acquisition controller 122 to select wavelength and verify current wavelength. Signal processor/conditioner 120 provides output via output connection 121 to data acquisition controller 122. Data acquisition controller 122 is connected via connection 123 to display 125. Data acquisition controller 122 may also provide output via connection 124 to an insulin or medication delivery device.

The above described instrument may also be used as non-invasive device for assessing changes in structural matrix, cells or mitochondria, or the environment of said components, or other cellular components reflective of metabolic activity, due to a variety of conditions including, for example, disease conditions (e.g. infections, cancer), the presence of topical chemicals such as steriods, age, photodamage, and combinations thereof which may provide the general state of health of the patient. This embodiment allows the assessment of changes in the structural matrix non-invasively by measuring the combination of fluorescence and scattering, and comparing these results to measurements of developed standards, temporal correlates or surrounding normal tissue. This device may be used to assess changes in the collagen matrix brought about by diseases such as diabetes, scleroderma, scarring, or atrophy induced by the use of steroids. It is also useful to assess changes in the matrix due to aging or photoaging and changes induced by long exposures to zero gravity environment. Treatment related changes and drug concentration monitoring are additional clinical and research applications. This embodiment may be miniaturized, and may be used clinically and in research applications to evaluate wound healing, protein metabolism, diabetes, collagen diseases and other conditions.

In addition to the analytical methodologies disclosed herein, other analytical methodologies may be incorporated into the various disclosed embodiments without departing from the spirit and scope of the invention. Useful methodologies include normalizations of spectra and multi variate analyses of all sorts. Multi variate analyses include PLS, PCR, LDA, MLR, stepwise LR, etc.

In the practice of the invention, factors such as age, UV damage, skin color, etc., can be accounted for in the analysis by correcting the spectra or by modeling it in such a way so as to account for these variations.

The collagen cross-links in the superficial or papillary dermis provide large fluorescence signals that are indicative of the state of the collagen matrix. These signals may be monitored non-invasively without interference with the functions of the skin. Specifically, as the matrix is irradiated with UVA, UVB or UVC radiation, the fluorescence of PDCCL decreases. This fluorescent effect recovers following a single exposure; however, the changes induced become permanent after multiple exposures. Degradation of PDC-CLs is wavelength dependent. The most effective wavelength range is UVA with a maximum decrease from 335 nm irradiation. 365 nm irradiation is much less effective than 335 nm.

The fluorescence signals from skin fluorescence with excitation in the UVA (320–400 nm) may be used to evaluate the state of the collagen matrix. In the skin and other tissues, as the collagen matrix is degraded due to the expression of matrix metalloproteinases, such as collagenase, in the stroma of tumors so does the fluorescence emission degrade from the collagenase digestible collagen cross links. By assessing fluorescence, it has been discovered that degenerative changes in the structural matrix or of matrix, cellular, or mitochondrial components, or other cellular components reflective of metabolic activity, may be assessed, such as changes induced by disease or environmental factors such as diabetes, age, photodamage, topical steroid application, or prolonged exposure to zero-gravity. Further, the intensity of scattered light by the dermis changes with aging and with changes in the collagen cross links. If the collagen cross links in the superficial or papillary dermis change, then the amount of light that is scattered by the dermis and its dependence on wavelength will also change. These changes may be monitored by reflectance.

Another aspect of the invention is related to a device that can measure either fluorescence excited at about 335 nm, fluorescence excited at about 370 nm, fluorescence excited at 460 nm, or a combination of all three, as well as the reflectance spectrum (280–1,100 nm), to thereby provide information on the state (or changes induced) of the structural matrix or environment of tissue matrix, cellular, or mitochondrial components, or other cellular components reflective of metabolic activity. By combining the assessment of fluorescence and scattering into one instrument, a novel device is provided that provides enhanced information on the state of the structural matrix or environment of tissue matrix components. Other wavelengths can also be used for excitation, such as a wavelength suitable for exciting tryptophan. A preferred embodiment incorporates a light source (Hg) and filters to select either 333 nm, 365 nm or visible broad band. The visible excitation may be provided by a tungsten halogen lamp of 1–2 watts or other source. The light is then conducted to the skin's surface by fibers, reflective optics or directly, and the fluorescence from the UVA excitations and the reflectance from the visible source are assessed with a photodiode array type of detectors. The fluorescence intensities can then be compared to standard signals from collagen samples (prepared from gelatin). The reflectance signal is analyzed for scattering and absorption by iterative methods at wavelengths of 280–820 nm.

Another aspect of the invention is related to an instrument for assessing changes in a structural, or the environment of, matrix, cellular, or mitochondrial components, or any other cellular component reflective of metabolic activity, of a patient comprising means for measuring fluorescence emitted from the skin, and means for measuring scattering. Optionally, the instrument may further comprise means for measuring absorbance. This embodiment may further include means for irradiating the tissue with a plurality of wavelengths of excitation light and means for synchronously scanning the fluorescence emitted from the skin with the excitation light.

The means for measuring fluorescence may comprise measuring one or more parameters selected from the group consisting of wavelength of fluorescence, overall fluorescence, relative peak ratios, spectral shapes, peak shifts, band narrowing and band broadening.

Another embodiment is directed to an instrument for assessing changes in the environment or the redox/metabolic state of the matrix, cellular, or mitochondrial components, or other cellular components reflective of metabolic activity, of a tissue comprising: means for measuring fluorescence; means for measuring scattering; and means for measuring absorbance. The instrument may further comprise means for determining changes in cellular and/or mitochondrial fluorophores.

Another embodiment is directed to a non-invasive method of assessing a change in the structural matrix, cellular, or mitochondrial components, or any other cellular component reflective of metabolic activity, of a tissue comprising: exposing the tissue to radiation at a first wavelength; detecting fluorescence emitted by exposed tissue; exposing the tissue to radiation of a second wavelength; detecting a scattering re-emitted from the exposed tissue; and deriving an indication representative of the change in the structural matrix of the tissue based on the fluorescence detected and the scattering detected. The method may further comprise the step of detecting absorbance.

The step of detecting fluorescence may comprise detecting one or more parameters selected from the group consisting of wavelength of fluorescence, intensity of fluorescence, overall fluorescence, relative peak ratios, spectral shapes, peak shifts, band narrowing and band broadening.

In a preferred embodiment, the first wavelength is ultraviolet radiation or is between about 320 and 420 nm, and the second wavelength may be between about 330 and 420 nm. Alternately, the first wavelength and the second wavelength may be the same. In another preferred embodiment, absorbance in the broad region using ultraviolet and visible radiation of 280–700 nm, or a smaller subset thereof, can be used. Important regions of this spectrum include, but are not limited to NADH (340 nm), Flavoproteins (370–500 nm), hemoglobin bands (oxy and deoxy) between 400 and 600 nm, and water bands in the NIR region.

Another embodiment is directed to a non-invasive method of assessing a change in the environment of the matrix, cellular, or mitochondrial components, or other cellular components reflective of metabolic activity, of a tissue comprising: exposing the tissue to radiation at a first wavelength; detecting fluorescence emitted by exposed tissue; exposing the tissue to radiation of a second wavelength; detecting scattering re-emitted from the exposed tissue; detecting absorbance; and deriving an indication representative of the change in the environment of the components of the tissue based on the fluorescence detected, the scattering detected and the absorbance detected.

Another embodiment is directed to a non-invasive method for monitoring skin or tissue constituents in which information about or signature of a specific blood analyte level or disease process is provided comprising the steps of exciting a target fluorophore; detecting radiation emitted by the fluorophore and transmitted through intervening tissue to the surface; and determining the information or signature from the radiation detected.

In addition to glucose, other parameters such as hematocrit, scarring, and healing may be monitored as desired using devices according to the invention. In order to enhance data collection, constant pressure may be used and the position of the fiber may be moved or varied after every scan to account for skin heterogeneity. In addition, synchronous scans and temperature monitoring may be incorporated as desired.

Reflectance spectra from subjects may be used as a means of determining data collection times. For example, by lengthening integration times spectra collected from darkly pigmented skin may be enhanced. Reflectance spectra may be used prior to fluorescence collection to determine the appropriate level of integration for that person's site.

The following examples are offered to illustrate embodiments of the present invention, but should not be viewed as limiting the scope of the invention.

EXAMPLES

Example 1

Glucose Levels of Diabetic versus Non-Diabetic Mice

Figure 3:
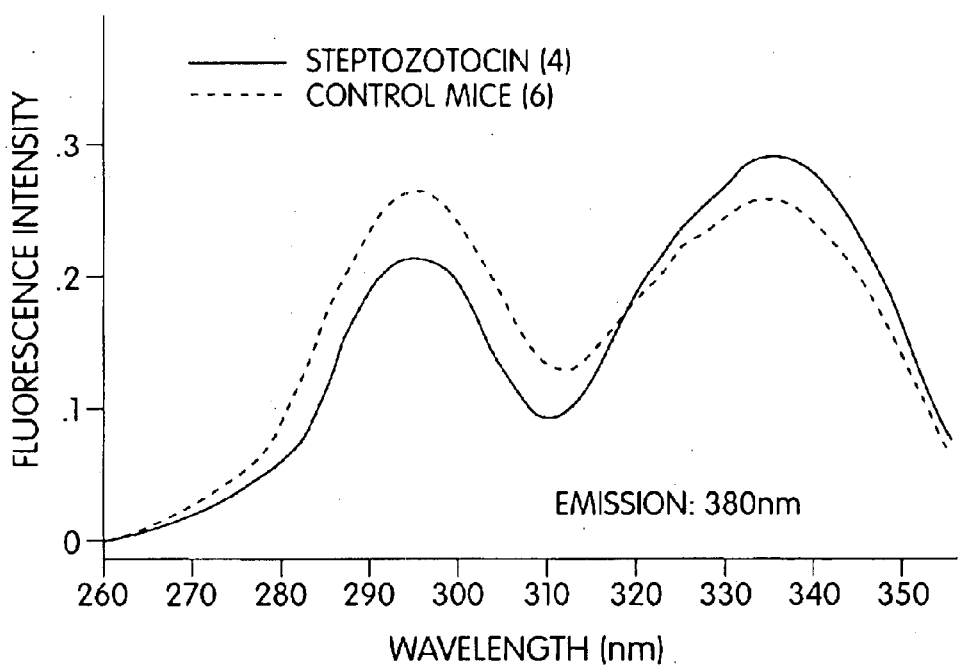
FIG. 3 Graph of the average fluorescence excitation spectra for normal and diabetic SKH mice for an emission wavelength of 380 nm.
Figure 4:
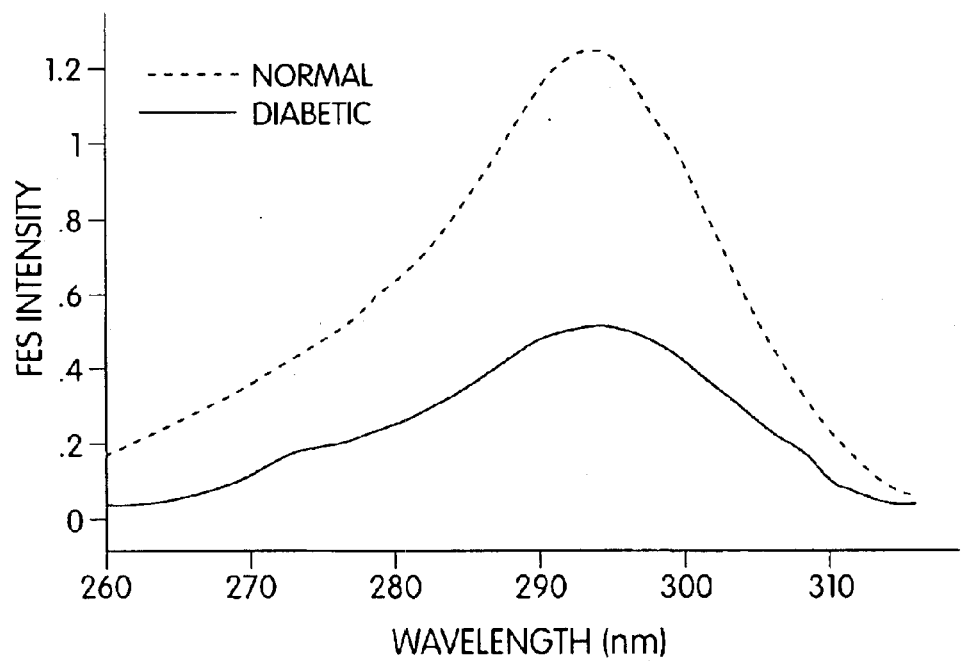
FIG. 4 Graph of the average fluorescence excitation spectra for normal and diabetic SKH mice for an emission wavelength of 340 nm.

Experiments were conducted for six hairless (SKH) diabetic mice made diabetic by the injection of streptozotocin, and six hairless (SKH) non-diabetic (normal) mice. Excitation spectra at emission wavelengths of 380 nm and 340 nm were collected for each of the twelve mice. A Xenon arc source coupled to a monochromator were fed into a fiber optic probe, which was then used to illuminate the backs of all of the mice at an intensity level of approximately 0.1–1.0 mW/cm$^2$. A spectrometer was used to collect the resulting spectra, which are shown in FIGS. 3 and 4 for emission at 380 nm and 340 nm, respectively. The plots indicate a significantly lower excitation intensity at 295 nm and a significantly higher excitation intensity at 340 nm for the diabetic mice. Urine collected from the animals confirmed that the glucose levels of the diabetic mice were higher at 340 nm for the diabetic mice.

Example 2

Glucose Levels of a Non-Diabetic Rat Following Ketamine and Insulin Treatments

Figure 5:
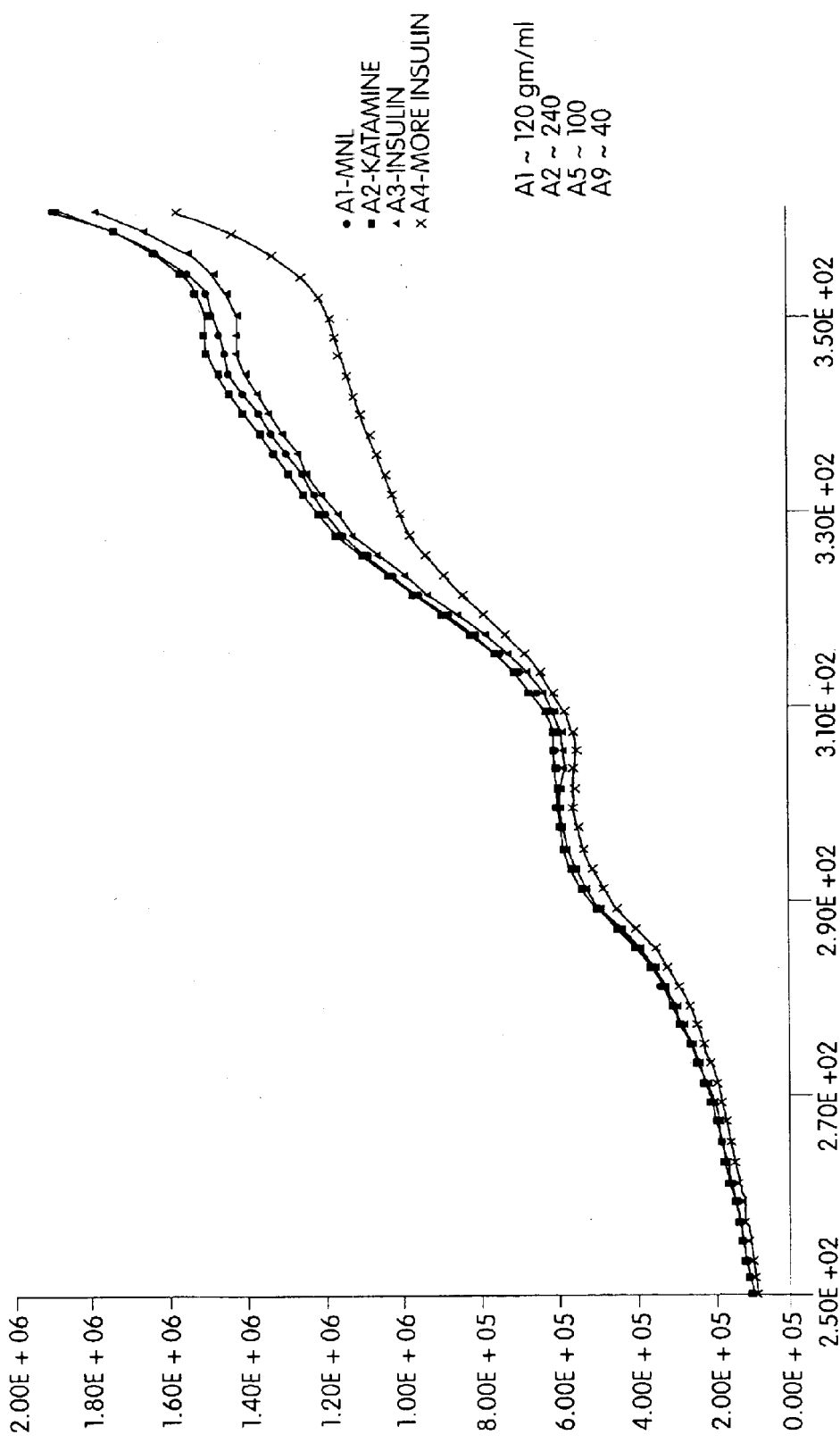
FIG. 5 Graph of the average fluorescence excitation spectra for a rat at an emission wavelength of 380 nm taken at different blood glucose levels.
Figure 6:
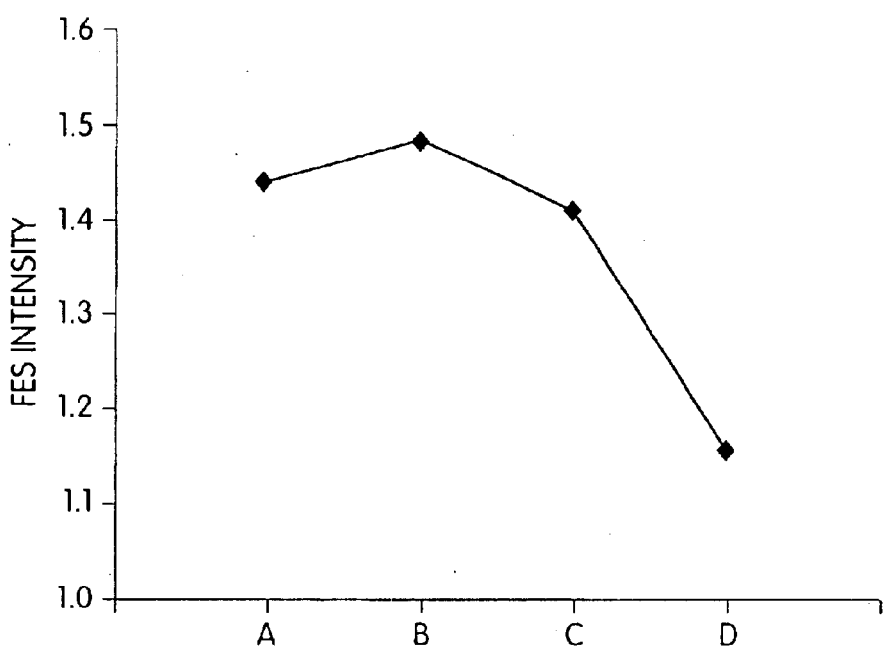
FIG. 6 Plot of the fluorescence intensity at 346 nm for four different glucose levels which are taken from FIG. 5.

Referring to FIG. 5, experiments were also conducted using a normal rat. The experimental apparatus used was the same as that used in Example 1. Fluorescence excitation spectra were obtained for the rat in the following situations, (A) at rest (diamonds), (B) after the administration of Ketamine (squares), (C) after the administration of insulin (triangles) and (D) after the administration of additional insulin (crosses). The glucose levels in situations A–D were determined to be 120, 240, 100, and 40 gm/ml, respectively. The results are believed to be superimposed on a light leakage signal that increases steadily with wavelength, although the use of double monochromators should eliminate this source of background noise. Spectra collected for this rat indicate that blood glucose level has a positive effect on fluorescence excitation in the 340 nm range. This is more clearly depicted in FIG. 6 in which the fluorescence excitation intensity at 346 nm for each of the situations A–D has been plotted.

Example 3

Glucose Levels of Human Subjects Before and After Glucose Ingestion

Figure 7:
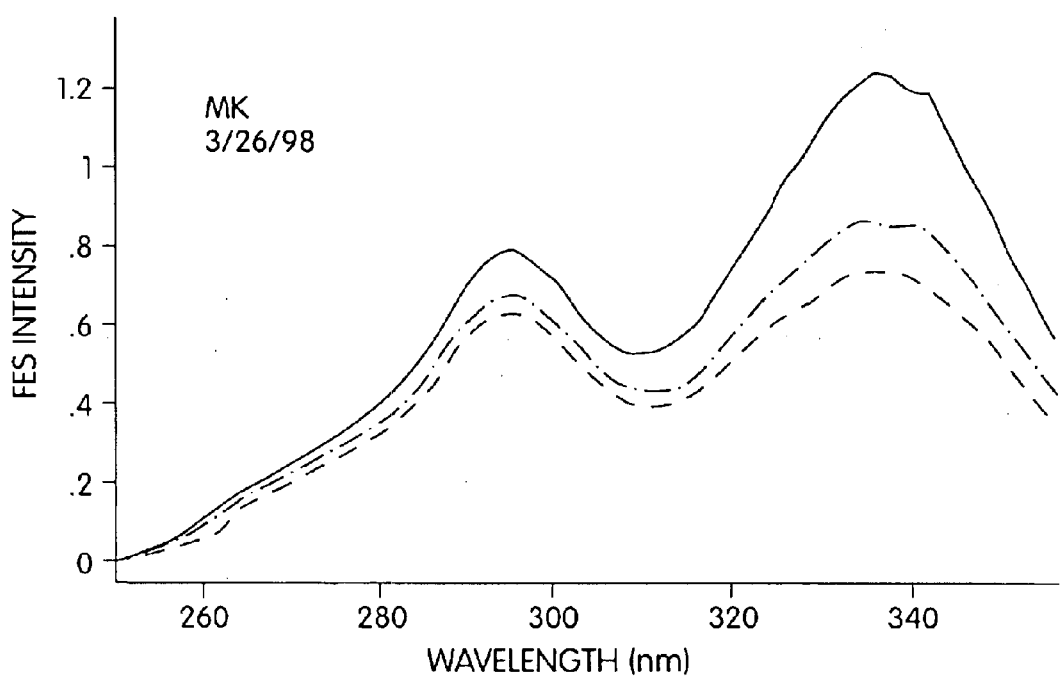
FIG. 7 Graph of the average fluorescence excitation spectra for an emission wavelength of 380 nm for a human male before and after the ingestion of 100 grams of glucose.
Figure 8:
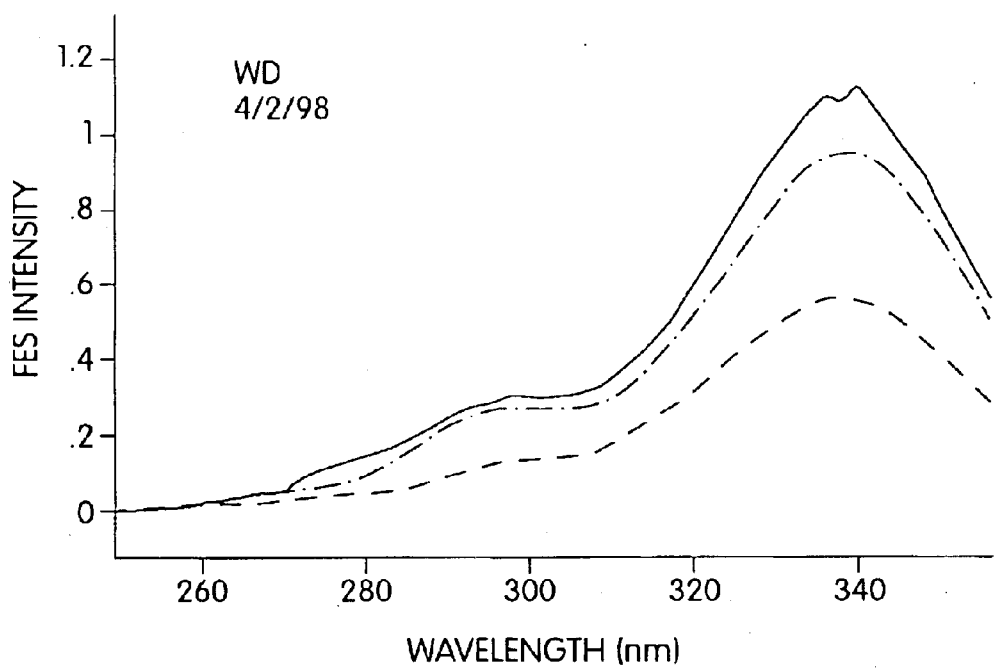
FIG. 8 Graph of the average fluorescence excitation spectra for an emission wavelength of 380 nm for a human male before and after the ingestion of 100 grams of glucose.
Figure 9:
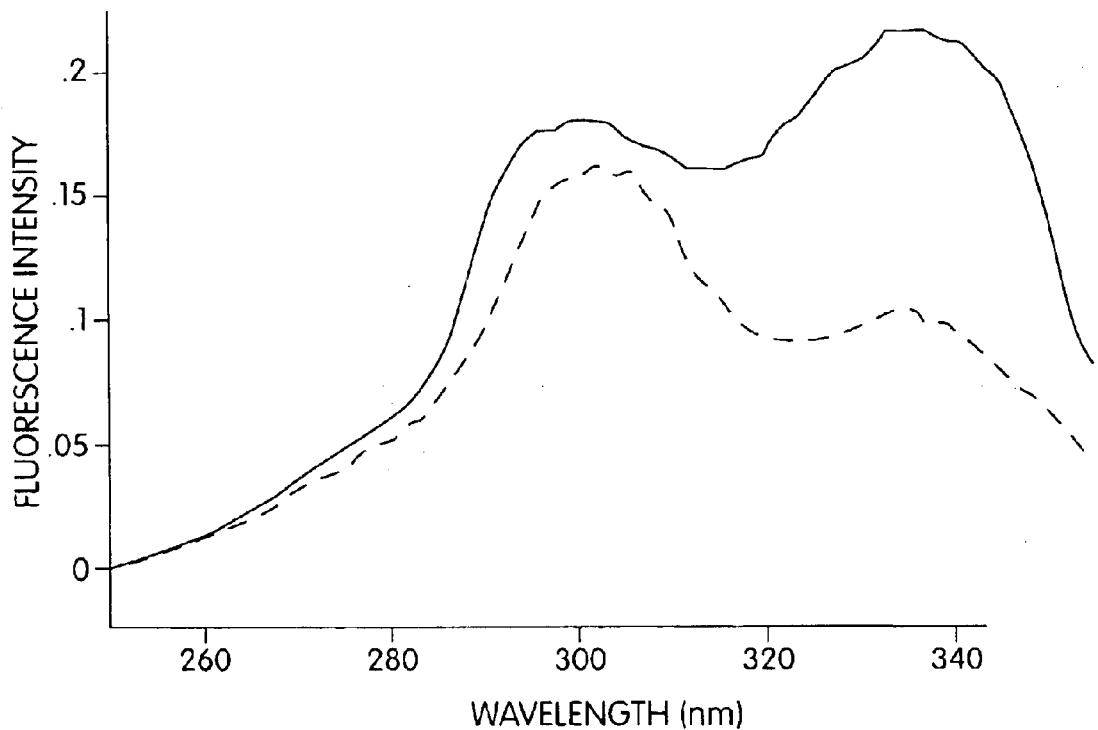
FIG. 9 Graph of the average fluorescence excitation spectra for an emission wavelength of 380 nm for a human female before and after the ingestion of 100 grams of glucose.

Preliminary experiments were also conducted on humans. FIGS. 7, 8 and 9 depict fluorescence excitation spectra for three human subjects, two males and one female, respectively, before (dashes), 30 minutes after (dotted/dashed line), and 50 minutes after (solid line) the ingestion of 100 grams of glucose. In each situation, the emission monochromator was set to a wavelength of 380 nm. Collagen and tryptophan spectra were found to change in ways similar to those for the animal models, although there appear to be individual differences. Dashed lines represent measurements before glucose intake. Dashed and dotted lines represent changes induced after glucose intake. Solid lines represent maximal changes induced by the intake of glucose.

Other embodiments and uses of the invention will be apparent to those skilled in the art from consideration of the specification and practice of the invention disclosed herein. As will be clear to those of skill in the art, the devices and methods of the present invention can be easily adapted to reflect or detect the level of a variety of substances in tissue, in addition to glucose and the described targets. All references cited herein, including all U.S. and foreign patents and patent applications, including, but not limited to, U.S. Patent Application titled "Multivariate Analysis of Green to Ultraviolet Spectra of Cell and Tissue Samples," U.S. patent application titled "Generation of Spatially-Averaged Excitation-Emission Map in Heterogeneous Tissue," U.S. patent application titled "Reduction of Inter-Subject Variation via Transfer Standardization," all filed contemporaneously herewith, are specifically and entirely hereby incorporated herein by reference. The specification and examples should be considered exemplary only with the true scope and spirit of the invention indicated by the following claims.

What is claimed is:

1. A non-invasive glucose monitoring instrument comprising:
   a radiation source for directing excitation radiation to a portion of a tissue surface wherein said source emits excitation radiation at a plurality of different wavelengths of ultraviolet or visible light that excites a target to emit radiation, such that the radiation emitted from the excited target and received at the tissue surface correlates with a glucose level of the tissue;
   a radiation detector positioned to receive the radiation emitted from the tissue surface, wherein the radiation detector is configured to synchronously scan radiation emitted by the target with the excitation radiation; and
   analyzing means operatively connected to the radiation detector for analyzing radiation detected by the radiation detector and translating said detected radiation to an indication of the tissue glucose level,
   wherein the target is selected from the group consisting of a structural matrix tissue component, a cellular tissue component, a mitochondrial tissue component, a collagen cross link, a pepsin-digestible collagen cross link, a collagenase-digestible collagen cross link, a non-pepsin digestible collagen cross link, an elastin cross link, a tryptophan-containing protein, NADH, FAD a flavoprotein, and any combination thereof.

2. The instrument of claim 1 which comprises a sync scan.

3. The instrument of claim 1 which comprises an excitation emission map.

4. The instrument of claim 1 where the included excitation wavelengths excite 370 nm and 460 nm.

5. The instrument of claim 1 wherein the radiation source is operative to emit radiation at between about 285 and 305 nm and the radiation detector is operative to detect radiation at between about 315 and 420 nm.

6. The instrument of claim 1 wherein the radiation source is operative to emit radiation at between about 330 and 345 nm and the radiation detector is operative to detect radiation at between about 370 and 410 nm.

7. The instrument of claim 1 wherein the radiation source is operative to emit radiation at between about 330 and 360 nm and the radiation detector is operative to detect radiation at between about 400 and 550 nm.

8. The instrument of claim 1 wherein the radiation source is operative to emit radiation at between about 330 and 500 nm and the radiation detector is operative to detect radiation at between about 500 and 560 nm.

9. The instrument of claim 1 further comprising a normalizing detector responsive to another target that provides normalizing information to said processing circuit to normalize the indicated glucose level.

10. The instrument of claim 1 further comprising normalizing means which provides normalizing information to said analyzing means to normalize the indicated glucose level.

11. The instrument of claim 10 wherein said normalizing means normalizes for age, UV damage, skin color, temperature, perfusion, hydration, pH and combinations thereof.

12. A non-invasive method of detecting a glucose level of a tissue comprising:
   exciting a non-glucose target in the tissue with ultraviolet radiation or visible light wherein the excited target emits radiation such that the radiation received at a tissue surface is indicative of a glucose level of a patient;
   detecting radiation emitted by the target and transmitted through the intervening tissue to the surface; and
   determining said glucose level from the radiation detected, wherein the excitation radiation is at two wavelengths of about 370 and 460 nm.

13. A non-invasive method of detecting a glucose level of a tissue comprising:
   exciting a non-glucose target in the tissue with ultraviolet radiation or visible light wherein the excited target emits radiation such that the radiation received at a tissue surface is indicative of a glucose level of a patient;
   detecting radiation emitted by the target and transmitted through the intervening tissue to the surface; and determining said glucose level from the radiation detected, wherein the excitation radiation is at a wavelength of about 590 nm.

14. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the excitation radiation is at a wavelength of about 670–680 nm.

15. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the excitation radiation is at two wavelengths of about 740 and 920 nm.

16. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the excitation radiation is a combination of subsets of the region of 280–1,100 nm.

17. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the radiation detected from the excited target is between about 340 and 400 nm.

18. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the radiation detected from the excited target is between about 400 and 550 nm.

19. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the radiation detected from the excited target is between about 500 and 560 nm.

20. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein the radiation detected from the excited target is a combination of subsets of the region of 340–560 nm.

21. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, the method further comprising normalizing the glucose level determined.

22. The method of claim 21 wherein normalizing comprises normalizing for one or more variables selected from the group consisting of temperature, degree of perfusion, age, UV damage, skin color temperature, hydration, and pH.

23. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, the method further comprising measuring scattering and absorbance and adjusting the glucose level.

24. A non-invasive method of detecting a glucose level of a tissue comprising:
exciting a non-glucose target in the tissue with ultraviolet radiation or visible light wherein the excited target emits radiation such that the radiation received at a tissue surface is indicative of a glucose level of a patient;
detecting radiation emitted by the target and transmitted through the intervening tissue to the surface; and
determining said glucose level from the radiation detected, wherein said step of determining the glucose level comprises analyzing the radiation detected using one or more multi variate analysis methodologies selected from a group comprising PLS, PCR, LDA, MLR, stepwise LR and combinations thereof.

25. A non-invasive method of detecting a glucose level of a tissue comprising:

exciting a non-glucose target in the tissue with ultraviolet radiation or visible light wherein the excited target emits radiation such that the radiation received at a tissue surface is indicative of a glucose level of a patient;

detecting radiation emitted by the target and transmitted through the intervening tissue to the surface; and determining said glucose level from the radiation detected, wherein said step of exciting comprises irradiating a target with excitation radiation at a plurality of wavelengths and the step of detecting radiation comprises the step of synchronously scanning the emitted radiation and excitation radiation.

26. A non-invasive method of detecting a glucose level of a tissue comprising:

exciting a non-glucose target in the tissue with ultraviolet radiation or visible light wherein the excited target emits radiation such that the radiation received at a tissue surface is indicative of a glucose level of a patient;

detecting radiation emitted by the target and transmitted through the intervening tissue to the surface; and determining said glucose level from the radiation detected, wherein the step of exciting comprises application of a probe to the skin, said probe comprising a radiation source and, wherein a position of the probe on the skin is varied during detecting.

* * * * *